United States Patent
Mysore Vishakante Gowda et al.

(10) Patent No.: US 10,555,988 B2
(45) Date of Patent: Feb. 11, 2020

(54) ANTIMICROBIAL PEPTIDES, THEIR VARIANTS AND USES

(71) Applicant: Chain Antimicrobials Oy, Oulu (FI)

(72) Inventors: Tejesvi Mysore Vishakante Gowda, Oulu (FI); Anna Maria Pirttilä, Oulu (FI)

(73) Assignee: Chain Antimicrobials Oy, Oulu (FI)

( * ) Notice: Subject to any disclaimer, the term of this patent is extended or adjusted under 35 U.S.C. 154(b) by 0 days.

(21) Appl. No.: 15/740,480

(22) PCT Filed: Jun. 29, 2016

(86) PCT No.: PCT/FI2016/050483
§ 371 (c)(1),
(2) Date: Dec. 28, 2017

(87) PCT Pub. No.: WO2017/001732
PCT Pub. Date: Jan. 5, 2017

(65) Prior Publication Data
US 2018/0193411 A1      Jul. 12, 2018

(30) Foreign Application Priority Data
Jun. 30, 2015   (FI) .................................... 20155517

(51) Int. Cl.
*A61K 38/16*    (2006.01)
*C07K 14/415*   (2006.01)
*A61P 31/04*    (2006.01)
*A61P 31/10*    (2006.01)

(52) U.S. Cl.
CPC ............ *A61K 38/168* (2013.01); *A61P 31/04* (2018.01); *A61P 31/10* (2018.01); *C07K 14/415* (2013.01)

(58) Field of Classification Search
CPC .............. C07K 14/4723; C07K 14/415; A61K 38/168; A61P 31/10; A61P 31/04
See application file for complete search history.

(56) References Cited

FOREIGN PATENT DOCUMENTS

| EP | 1051433 B1 | 10/2004 |
|----|------------|---------|
| EP | 2404932 B1 | 7/2014 |
| WO | 2011113999 A1 | 9/2011 |

OTHER PUBLICATIONS

Park et al, Synthetic Diastereomeric-Antimicrobial Peptide: Antibacterial Activity against Multiple Drug Resistant Clinical Isolates, Peptide Science, 2011, 96, pp. 130-136.*
Sequence listing of WO 2011/113999 A1, pp. 1-13.*
Wang et al, APD3: the antimicrobial peptide database as a tool for research and education, Nucleic Acids Research, 2016, 44, pp. D1087-D1093.*
Saravanan Rathi et el; Design of Short Membrane Selective Antimicrobial Peptides Containing Tryptophan and Arginine Residues for Improved Activity, Salt-Resistance, and Biocompatibility; Biotechnology and Bioengineering, Jan. 2014; vol. 111, No. 1, pp. 37-49.
Shang Dejing et el; Design of Potent, Non-Toxic Antimicrobial Agents Based upon the Structure of the Frog Skin Peptide, Temporin-1CEb from the Chinese Brown Frog, Rana chensinensis; Chemical Biology Drug Design, May 2012; vol. 79, No. 5, pp. 653-662.
Search report of Finnish Patent application FI-20155517; issued by Finnish Patent and Registration office dated Feb. 8, 2016, 4 pages.
International search report and Written Opinion of PCT/FI2016/050483 issued by European Patent Office dated Sep. 21, 2016, 11 pages.
Database UniProt (Online); Mar. 19, 2014; Subname: Full=CRISPR-associated protein, XP0002761512; retrieved from EBI accession No. UniProt:W1V035 Dababase accession No. W1V035, 1 page.
Shin Soyoung et al; Design of potent 9-mer antimicrobial peptide analogs of protaetiamycine and investigtaion of mechanism of antimicrobial action; Journal of Peptide Science, John Wiley and Sons Ltd, GB, vol. 15, No. 9, SP, Iss, SI, Sep. 1, 2009, pp. 559-568.
Database EPO Proteins (Online); Oct. 18, 2011; Sequence 4 from Patent WO201111399; XP002761263, retrieved from EBI accession No. EPOP:JA610562 Dabase accession No. JA610562 sequence, 1 page.
Haug B E et al; The medicinal chemistry of short lactoferricing-based antibacterial peptides; Current Medicinal Chemistry: The new international Journal for Timely in-depth reviews in medicinal chemistry, Bentham, NL, vol. 14, No. 1; Jan. 1, 2007.
Waghu Faiza Hanif et al: CAMP: Collection of sequences and structures of antimicrobial peptides; Nucleic Acids Research, Oxford University Press, GB, vol. 42, Dabase issue, Jan. 1, 2014, pp. D1154-D1158.

* cited by examiner

*Primary Examiner* — Karlheinz R. Skowronek
*Assistant Examiner* — Li N Komatsu
(74) *Attorney, Agent, or Firm* — Berggren LLP

(57) ABSTRACT

The present invention relates to novel antimicrobial peptide and variants thereof. The invention further relates to method of killing or inhibiting growth of microbes and use of the peptide here disclosed as a medicament, feed additive, preservative or surfactant.

8 Claims, 17 Drawing Sheets
Specification includes a Sequence Listing.

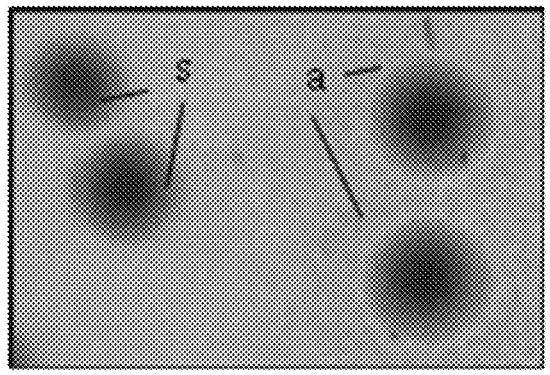

Fig. 1

MRLVAHPVPDAPLYALMIKACSMGIPQPNDNLWKPRNPLLAKEEKTSKR
GRTAPDTERALDLFREMTLRYNIRPTAEVYTAIIAACVKRDDMYDKGFG
LFKKMVELERNRMSSEGHDSTSFAPTRATYNALLRGCARNKDLLRARWI
LAEMLRTAQAKWQEFMEKSKKGEEGVQEWELLEVEEMRPDTNTMAFLFY
TYASHTTSSKAVPETEGKKELEGKAEERASEVTSVSPVSEPPEPMDESK
LVYSLPTSSQAILREVTSLLDRIKSDQGQQSNLLSSVQINSKLLNSYIA
VLSAHCRSSQVVERISEVVVGTKENPKSLFEETGTSVNGYTCFTVIDAC
GMMEHSPDTYHLACEMWQRWLSLVENATFHRENPLKAKEIGLDSRTISD
CWSAMIRLHAKYNQVDEAMKLVHEFARLYPPASLFNSLTFEPSSTSSSS
LSPRKGVQEISPLFSSTSLTHSIRGRDISRIQNTMSQDPTLQFRAVQIL
HLRLVELETRPKDLAYLSWLLKSYEHQLQPKRPKSLQGDLFTSRQAAYN
RIVQQRTSSR      SEQ ID NO: 1

Fig. 2

| | | |
|---|---|---|
| Chain100 | RKWSAMIRLHAKYNQV | SEQ ID NO: 6 |
| Chain101 | -------KIRLHRKRLRK | SEQ ID NO: 7 |
| Chain102 | -------KKRLHRKRLRK | SEQ ID NO: 8 |
| Chain103 | -------KLRLHAKRLRK | SEQ ID NO: 9 |
| Chain104 | RKWRAMIRLHAKRLRK | SEQ ID NO: 10 |
| Chain105 | RKWRAMIRLHAKWLRK | SEQ ID NO: 11 |
| Chain106 | -------WIRLHRKRLRK | SEQ ID NO: 12 |
| Chain107 | -------WWRLHAKKKLW | SEQ ID NO: 13 |
| Chain108 | -------WWRLHAKRKLW | SEQ ID NO: 14 |
| Chain109 | -------WWRLHAKWKLW | SEQ ID NO: 15 |
| Chain110 | RLKRAMIRLHAKKRLK | SEQ ID NO: 16 |
| Chain111 | RLKRAMIRLHAKKWRW | SEQ ID NO: 17 |
| Chain112 | RLKRAMIRLHAKKWRW | SEQ ID NO: 18 |
| Chain113 | RWWRAMIRLHAKKWRW | SEQ ID NO: 19 |
| Chain114 | -------WWRLHAKKKIL | SEQ ID NO: 20 |
| Chain115 | -------WWRLHAKKKCW | SEQ ID NO: 21 |
| Chain116 | -------WWRLHAKKKFW | SEQ ID NO: 22 |
| Chain117 | -------WWRLHAKKKIW | SEQ ID NO: 23 |
| Chain118 | -------WWRLHAKKKRW | SEQ ID NO: 24 |
| Chain119 | -------WWRLHAKKKWW | SEQ ID NO: 25 |
| Chain120 | -------WWRLHAKKKWW | SEQ ID NO: 26 |
| Chain121 | -------WWRLHAKLKLW | SEQ ID NO: 27 |
| Chain122 | -------WWRLHAKKKRW | SEQ ID NO: 28 |
| Chain123 | -------WWRLHAKKWRW | SEQ ID NO: 29 |
| Chain124 | -------WWRLHAKKIWW | SEQ ID NO: 30 |
| Chain125 | -------WWRLHAKKWRR | SEQ ID NO: 31 |

Fig. 4a

| | | |
|---|---|---|
| Chain201 | KKIVWRW-RFKR- | SEQ ID NO: 32 |
| Chain212 | KRWRKWR-LFKR- | SEQ ID NO: 43 |
| Chain204 | RRLIWRRFKWLR- | SEQ ID NO: 35 |
| Chain200 | NRIVQQR-TSSR- | SEQ ID NO: 5 |
| Chain203 | RRIVKLR-WFKR- | SEQ ID NO: 34 |
| Chain218 | RRIVRKK-TFKR- | SEQ ID NO: 49 |
| Chain222 | WKIVKKR-TRRR- | SEQ ID NO: 53 |
| Chain205 | KRIVRWR-TRKR- | SEQ ID NO: 36 |
| Chain206 | KRIVRWR-WRKR- | SEQ ID NO: 37 |
| Chain208 | WRILRWR-KLRR- | SEQ ID NO: 39 |
| Chain207 | KRIVRWR-KLRRK | SEQ ID NO: 38 |
| Chain210 | WRIVQWR-KLKR- | SEQ ID NO: 41 |
| Chain209 | WRIVRWR-KLKR- | SEQ ID NO: 40 |
| Chain211 | KRIVRRR-TFKR- | SEQ ID NO: 42 |
| Chain223 | WRIVRRR-TFKR- | SEQ ID NO: 54 |
| Chain219 | RRIVWRR-TFKR- | SEQ ID NO: 50 |
| Chain220 | RWIVQRR-TFKR- | SEQ ID NO: 51 |
| Chain217 | RLIVRRR-TFKR- | SEQ ID NO: 48 |
| Chain221 | RVIVRRR-TFKR- | SEQ ID NO: 52 |
| Chain213 | NRIVLLR-TFKR- | SEQ ID NO: 44 |
| Chain214 | NRIVKKR-TFKR- | SEQ ID NO: 45 |
| Chain202 | RKIVKKR-TFKR- | SEQ ID NO: 33 |
| Chain215 | RKIVKRR-TFKR- | SEQ ID NO: 46 |
| Chain216 | RKIVWWR-TFKR- | SEQ ID NO: 47 |

Fig. 4b

```
Chain300     YDKGFGLFKK-M    SEQ ID NO:4
Chain301     IIKRFRLFK-KL    SEQ ID NO:35
Chain302     ILKRWWLFKK-L    SEQ ID NO:36
Chain303     IWKRFRLFK-KR    SEQ ID NO:37
Chain304     IWKRFRLFK-KW    SEQ ID NO:38
Chain305     RLKWFWLRKL-K    SEQ ID NO:39
Chain306     RLKRWRLFR-KR    SEQ ID NO:60
Chain307     RLKWFWLFRK-R    SEQ ID NO:61
Chain308     RLKWFLLFRK-R    SEQ ID NO:62
Chain309     WRKWFWLFKK-R    SEQ ID NO:63
Chain310     KRKWRWLFKK-L    SEQ ID NO:64
Chain311     KLKWFWLFKK-R    SEQ ID NO:65
Chain312     KLKKFKLFK-KR    SEQ ID NO:66
Chain313     RLKRFRLFRKRK    SEQ ID NO:67
Chain314     KRKRFRLFK-KR    SEQ ID NO:68
Chain315     RLKRFRLFK-KL    SEQ ID NO:69
Chain316     RRKRFRLFK-KM    SEQ ID NO:70
Chain317     RRKRFRLFR-RK    SEQ ID NO:71
Chain318     RWKRFRLFK-KR    SEQ ID NO:72
Chain319     RWKRFRLFK-KW    SEQ ID NO:73
Chain320     WKKGFGLFKK-M    SEQ ID NO:74
Chain321     WKKRFRLFK-KL    SEQ ID NO:75
Chain322     WLRRFRLFR-RL    SEQ ID NO:76
Chain323     RLKRFLLFRKRL    SEQ ID NO:77
Chain324     KRKWFWLFKK-L    SEQ ID NO:78
Chain325     KLKRFRLFK-KR    SEQ ID NO:79
```

Fig. 4c

```
Chain100     DCWSAMIRLHAKYNQV    SEQ ID NO:4
Chain101     ------KIRLHRKRLRK    SEQ ID NO:7
Chain102     ------KKRLHRKRLRK    SEQ ID NO:8
Chain103     ------KLRLHAKRLRK    SEQ ID NO:9
Chain104     RKWRAMIRLHAKRLRK    SEQ ID NO:10
Chain105     RKWRAMIRLHAKWLRK    SEQ ID NO:11
Chain106     ------WIRLHWKRLRK    SEQ ID NO:12
Chain107     ------WWRLHAKKKLW    SEQ ID NO:13
Chain108     ------WWRLHAKRKLW    SEQ ID NO:14
Chain109     ------WWRLHAKWKLW    SEQ ID NO:15
```

Fig. 5a

| Chain200 | WRIVQQRT-SS-R | SEQ ID NO: 5 |
| Chain201 | KWIVWRWK-FK-R | SEQ ID NO: 32 |
| Chain202 | RRIVKKRT-FK-R | SEQ ID NO: 33 |
| Chain203 | RRIVKLRW-FK-R | SEQ ID NO: 34 |
| Chain204 | RRLIWRRFKWL-R | SEQ ID NO: 35 |
| Chain205 | KRIVRWRT-RK-R | SEQ ID NO: 36 |
| Chain206 | KRIVRWRW-RK-R | SEQ ID NO: 37 |
| Chain207 | KRIVRWRK-LKRK | SEQ ID NO: 38 |
| Chain208 | WRILRWRK-LK-R | SEQ ID NO: 39 |
| Chain209 | WRIVRWRK-LK-R | SEQ ID NO: 40 |
| Chain210 | WRIVQWRK-LK-R | SEQ ID NO: 41 |

Fig. 5b

| Chain300 | YDKGFGLFK-KM | SEQ ID NO: 6 |
| Chain301 | IIKRFRLFK-KL | SEQ ID NO: 55 |
| Chain302 | ILKRWWLFK-KL | SEQ ID NO: 56 |
| Chain303 | IWKRFRLFK-KR | SEQ ID NO: 57 |
| Chain304 | IWKRFRLFK-KW | SEQ ID NO: 58 |
| Chain305 | RLKWFWLRK-LK | SEQ ID NO: 59 |
| Chain306 | RLKRWRLFR-KR | SEQ ID NO: 60 |
| Chain307 | RLKWFWLFR-KR | SEQ ID NO: 61 |
| Chain308 | RLKWFLLFR-KR | SEQ ID NO: 62 |
| Chain309 | WRKWFWLFK-KR | SEQ ID NO: 63 |
| Chain310 | KRKWRWLFK-KL | SEQ ID NO: 64 |
| Chain311 | KLKWFWLFK-KR | SEQ ID NO: 65 |
| Chain312 | RLKKFKLFK-KR | SEQ ID NO: 66 |
| Chain313 | RLKRFRLFRKRK | SEQ ID NO: 67 |

SEQUENCE LISTING

```
<160> NUMBER OF SEQ ID NOS: 80

<210> SEQ ID NO 1
<211> LENGTH: 549
<212> TYPE: PRT
<213> ORGANISM: Empetrum nigrum

<400> SEQUENCE: 1

Met Arg Leu Val Ala His Pro Val Pro Asp Ala Pro Leu Tyr Ala Leu
1               5                   10                  15

Met Ile Lys Ala Cys Ser Met Gly Ile Pro Gln Pro Asn Asp Asn Leu
            20                  25                  30

Trp Lys Pro Arg Asn Pro Leu Leu Ala Lys Glu Glu Lys Thr Ser Lys
        35                  40                  45

Arg Gly Arg Thr Ala Pro Asp Thr Glu Arg Ala Leu Asp Leu Phe Arg
    50                  55                  60

Glu Met Thr Leu Arg Tyr Asn Ile Arg Pro Thr Ala Glu Val Tyr Thr
65                  70                  75                  80

Ala Ile Ile Ala Ala Cys Val Lys Arg Asp Asp Met Tyr Asp Lys Gly
                85                  90                  95

Phe Gly Leu Phe Lys Lys Met Val Glu Leu Glu Arg Asn Arg Met Ser
            100                 105                 110

Ser Glu Gly His Asp Ser Thr Ser Phe Ala Pro Thr Arg Ala Thr Tyr
        115                 120                 125

Asn Ala Leu Leu Arg Gly Cys Ala Arg Asn Lys Asp Leu Leu Arg Ala
    130                 135                 140

Arg Trp Ile Leu Ala Glu Met Leu Arg Thr Ala Gln Ala Lys Trp Gln
```

```
           145                 150                 155                 160
       Glu Phe Met Glu Lys Ser Lys Lys Gly Glu Glu Gly Val Gln Glu Trp
                       165                 170                 175

Glu Leu Leu Glu Val Glu Glu Met Arg Pro Asp Thr Asn Thr Met Ala
                       180                 185                 190

Phe Leu Phe Tyr Thr Tyr Ala Ser His Thr Thr Ser Ser Lys Ala Val
                       195                 200                 205

Pro Glu Thr Glu Gly Lys Lys Glu Leu Glu Gly Lys Ala Glu Glu Arg
       210                 215                 220

Ala Ser Glu Val Thr Ser Val Ser Pro Val Ser Glu Pro Pro Glu Pro
       225                 230                 235                 240

Met Asp Glu Ser Lys Leu Val Tyr Ser Leu Pro Thr Ser Ser Gln Ala
                       245                 250                 255

Ile Leu Arg Glu Val Thr Ser Leu Leu Asp Arg Ile Lys Ser Asp Gln
                       260                 265                 270

Gly Gln Gln Ser Asn Leu Leu Ser Ser Val Gln Ile Asn Ser Lys Leu
                       275                 280                 285

Leu Asn Ser Tyr Ile Ala Val Leu Ser Ala His Cys Arg Ser Ser Gln
                       290                 295                 300

Val Val Glu Arg Ile Ser Glu Val Val Gly Thr Lys Glu Asn Pro
       305                 310                 315                 320

Lys Ser Leu Phe Glu Glu Thr Gly Thr Ser Val Asn Gly Tyr Thr Cys
                       325                 330                 335

Phe Thr Val Ile Asp Ala Cys Gly Met Met Glu His Ser Pro Asp Thr
                       340                 345                 350

Tyr His Leu Ala Cys Glu Met Trp Gln Arg Trp Leu Ser Leu Val Glu
                       355                 360                 365

Asn Ala Thr Phe His Arg Glu Asn Pro Leu Lys Ala Lys Glu Ile Gly
                       370                 375                 380

Leu Asp Ser Arg Thr Ile Ser Asp Cys Trp Ser Ala Met Ile Arg Leu
       385                 390                 395                 400

His Ala Lys Tyr Asn Gln Val Asp Glu Ala Met Lys Leu Val His Glu
                       405                 410                 415

Phe Ala Arg Leu Tyr Pro Pro Ala Ser Leu Phe Asn Ser Leu Thr Phe
                       420                 425                 430

Glu Pro Ser Ser Thr Ser Ser Ser Leu Ser Pro Arg Lys Gly Val
                       435                 440                 445

Gln Glu Ile Ser Pro Leu Phe Ser Ser Thr Leu Thr His Ser Ile
                       450                 455                 460

Arg Gly Arg Asp Ile Ser Arg Ile Gln Asn Thr Met Ser Gln Asp Pro
       465                 470                 475                 480

Thr Leu Gln Phe Arg Ala Val Gln Ile Leu His Leu Arg Leu Val Glu
                       485                 490                 495

Leu Glu Thr Arg Pro Lys Asp Leu Ala Tyr Leu Ser Trp Leu Leu Lys
                       500                 505                 510

Ser Tyr Glu His Gln Leu Gln Pro Lys Arg Pro Lys Ser Leu Gln Gly
                       515                 520                 525

Asp Leu Phe Thr Ser Arg Gln Ala Ala Tyr Asn Arg Ile Val Gln Gln
                       530                 535                 540

Arg Thr Ser Ser Arg
       545

<210> SEQ ID NO 2
```

```
<211> LENGTH: 35
<212> TYPE: DNA
<213> ORGANISM: Artificial Sequence
<220> FEATURE:
<223> OTHER INFORMATION: primer

<400> SEQUENCE: 2
catatgagac tagtagctca tcctgttcct gatgc                              35

<210> SEQ ID NO 3
<211> LENGTH: 37
<212> TYPE: DNA
<213> ORGANISM: Artificial Sequence
<220> FEATURE:
<223> OTHER INFORMATION: primer

<400> SEQUENCE: 3
gtcgacttat taacgagatg acgtcctctg ctgtacg                            37

<210> SEQ ID NO 4
<211> LENGTH: 16
<212> TYPE: PRT
<213> ORGANISM: artificial
<220> FEATURE:
<223> OTHER INFORMATION: peptide

<400> SEQUENCE: 4

Asp Cys Trp Ser Ala Met Ile Arg Leu His Ala Lys Tyr Asn Gln Val
1               5                   10                  15

<210> SEQ ID NO 5
<211> LENGTH: 11
<212> TYPE: PRT
<213> ORGANISM: Artificial Sequence
<220> FEATURE:
<223> OTHER INFORMATION: peptide

<400> SEQUENCE: 5

Asn Arg Ile Val Gln Gln Arg Thr Ser Ser Arg
1               5                   10

<210> SEQ ID NO 6
<211> LENGTH: 11
<212> TYPE: PRT
<213> ORGANISM: Artificial Sequence
<220> FEATURE:
<223> OTHER INFORMATION: peptide

<400> SEQUENCE: 6

Tyr Asp Lys Gly Phe Gly Leu Phe Lys Lys Met
1               5                   10

<210> SEQ ID NO 7
<211> LENGTH: 11
<212> TYPE: PRT
<213> ORGANISM: Artificial Sequence
<220> FEATURE:
<223> OTHER INFORMATION: peptide (101)

<400> SEQUENCE: 7

Lys Ile Arg Leu His Arg Lys Arg Leu Arg Lys
1               5                   10

<210> SEQ ID NO 8
<211> LENGTH: 11
<212> TYPE: PRT
<213> ORGANISM: Artificial Sequence
```

-continued

<220> FEATURE:
<223> OTHER INFORMATION: peptide (102)

<400> SEQUENCE: 8

Lys Lys Arg Leu His Arg Lys Arg Leu Arg Lys
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Ppeptide (103)

<400> SEQUENCE: 9

Lys Leu Arg Leu His Ala Lys Arg Leu Arg Lys
1               5                   10

<210> SEQ ID NO 10
<211> LENGTH: 16
<212> TYPE: PRT
<213> ORGANISM: Artificial Sequence
<220> FEATURE:
<223> OTHER INFORMATION: peptide (104)

<400> SEQUENCE: 10

Arg Lys Trp Arg Ala Met Ile Arg Leu His Ala Lys Arg Leu Arg Lys
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Peptide (105)

<400> SEQUENCE: 11

Arg Lys Trp Arg Ala Met Ile Arg Leu His Ala Lys Trp Leu Arg Lys
1               5                   10                  15

<210> SEQ ID NO 12
<211> LENGTH: 11
<212> TYPE: PRT
<213> ORGANISM: Artificial Sequence
<220> FEATURE:
<223> OTHER INFORMATION: peptide (106)

<400> SEQUENCE: 12

Trp Ile Arg Leu His Trp Lys Arg Leu Arg Lys
1               5                   10

<210> SEQ ID NO 13
<211> LENGTH: 11
<212> TYPE: PRT
<213> ORGANISM: Artificial Sequence
<220> FEATURE:
<223> OTHER INFORMATION: peptide (107)

<400> SEQUENCE: 13

Trp Trp Arg Leu His Ala Lys Lys Lys Leu Trp
1               5                   10

<210> SEQ ID NO 14
<211> LENGTH: 11
<212> TYPE: PRT
<213> ORGANISM: Artificial Sequence
<220> FEATURE:

<223> OTHER INFORMATION: peptide (108)

<400> SEQUENCE: 14

Trp Trp Arg Leu His Ala Lys Arg Lys Leu Trp
1               5                   10

<210> SEQ ID NO 15
<211> LENGTH: 11
<212> TYPE: PRT
<213> ORGANISM: Artificial Sequence
<220> FEATURE:
<223> OTHER INFORMATION: peptide (109)

<400> SEQUENCE: 15

Trp Trp Arg Leu His Ala Lys Trp Lys Leu Trp
1               5                   10

<210> SEQ ID NO 16
<211> LENGTH: 16
<212> TYPE: PRT
<213> ORGANISM: Artificial Sequence
<220> FEATURE:
<223> OTHER INFORMATION: peptide (110)

<400> SEQUENCE: 16

Lys Leu Lys Arg Ala Met Ile Arg Leu His Ala Lys Lys Arg Leu Lys
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: peptide (111)

<400> SEQUENCE: 17

Lys Leu Lys Arg Ala Met Ile Arg Leu His Ala Lys Lys Trp Arg Trp
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: peptide (112)

<400> SEQUENCE: 18

Arg Leu Lys Arg Ala Met Ile Arg Leu His Ala Lys Lys Trp Arg Trp
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: peptide (113)

<400> SEQUENCE: 19

Arg Trp Trp Arg Ala Met Ile Arg Leu His Ala Lys Lys Trp Arg Trp
1               5                   10                  15

<210> SEQ ID NO 20
<211> LENGTH: 11
<212> TYPE: PRT
<213> ORGANISM: Artificial Sequence
<220> FEATURE:
<223> OTHER INFORMATION: peptide (114)

-continued

```
<400> SEQUENCE: 20

Trp Trp Arg Leu His Ala Ala Lys Lys Ile Leu
1               5                   10

<210> SEQ ID NO 21
<211> LENGTH: 11
<212> TYPE: PRT
<213> ORGANISM: Artificial Sequence
<220> FEATURE:
<223> OTHER INFORMATION: peptide (115)

<400> SEQUENCE: 21

Trp Trp Arg Leu His Ala Lys Lys Lys Cys Trp
1               5                   10

<210> SEQ ID NO 22
<211> LENGTH: 11
<212> TYPE: PRT
<213> ORGANISM: Artificial Sequence
<220> FEATURE:
<223> OTHER INFORMATION: peptide (116)

<400> SEQUENCE: 22

Trp Trp Arg Leu His Ala Lys Lys Lys Phe Trp
1               5                   10

<210> SEQ ID NO 23
<211> LENGTH: 11
<212> TYPE: PRT
<213> ORGANISM: Artificial Sequence
<220> FEATURE:
<223> OTHER INFORMATION: peptide (117)

<400> SEQUENCE: 23

Trp Trp Arg Leu His Ala Lys Lys Lys Ile Trp
1               5                   10

<210> SEQ ID NO 24
<211> LENGTH: 11
<212> TYPE: PRT
<213> ORGANISM: Artificial Sequence
<220> FEATURE:
<223> OTHER INFORMATION: peptide (118)

<400> SEQUENCE: 24

Trp Trp Arg Leu His Ala Lys Lys Lys Arg Trp
1               5                   10

<210> SEQ ID NO 25
<211> LENGTH: 11
<212> TYPE: PRT
<213> ORGANISM: Artificial Sequence
<220> FEATURE:
<223> OTHER INFORMATION: peptide (119)

<400> SEQUENCE: 25

Trp Trp Arg Leu His Ala Lys Lys Lys Trp Arg
1               5                   10

<210> SEQ ID NO 26
<211> LENGTH: 11
<212> TYPE: PRT
<213> ORGANISM: Artificial Sequence
<220> FEATURE:
<223> OTHER INFORMATION: peptide (120)
```

<400> SEQUENCE: 26

Trp Trp Arg Leu His Ala Lys Lys Lys Trp Trp
1               5                   10

<210> SEQ ID NO 27
<211> LENGTH: 11
<212> TYPE: PRT
<213> ORGANISM: Artificial Sequence
<220> FEATURE:
<223> OTHER INFORMATION: peptide (121)

<400> SEQUENCE: 27

Trp Trp Arg Leu His Ala Lys Leu Lys Leu Trp
1               5                   10

<210> SEQ ID NO 28
<211> LENGTH: 11
<212> TYPE: PRT
<213> ORGANISM: Artificial Sequence
<220> FEATURE:
<223> OTHER INFORMATION: peptide (122)

<400> SEQUENCE: 28

Trp Trp Arg Leu His Ala Lys Arg Lys Arg Trp
1               5                   10

<210> SEQ ID NO 29
<211> LENGTH: 11
<212> TYPE: PRT
<213> ORGANISM: Artificial Sequence
<220> FEATURE:
<223> OTHER INFORMATION: peptide (123)

<400> SEQUENCE: 29

Trp Trp Arg Leu His Ala Lys Trp Arg Trp Arg
1               5                   10

<210> SEQ ID NO 30
<211> LENGTH: 11
<212> TYPE: PRT
<213> ORGANISM: Artificial Sequence
<220> FEATURE:
<223> OTHER INFORMATION: peptide (124)

<400> SEQUENCE: 30

Trp Trp Arg Leu His Ala Arg Lys Arg Trp Trp
1               5                   10

<210> SEQ ID NO 31
<211> LENGTH: 11
<212> TYPE: PRT
<213> ORGANISM: Artificial Sequence
<220> FEATURE:
<223> OTHER INFORMATION: peptide (125)

<400> SEQUENCE: 31

Trp Trp Arg Leu His Ala Trp Lys Trp Arg Arg
1               5                   10

<210> SEQ ID NO 32
<211> LENGTH: 11
<212> TYPE: PRT
<213> ORGANISM: Artificial Sequence
<220> FEATURE:
<223> OTHER INFORMATION: peptide (201)

<400> SEQUENCE: 32

```
Lys Trp Ile Val Trp Arg Trp Arg Phe Lys Arg
1               5                   10
```

<210> SEQ ID NO 33
<211> LENGTH: 11
<212> TYPE: PRT
<213> ORGANISM: Artificial Sequence
<220> FEATURE:
<223> OTHER INFORMATION: peptide (202)

<400> SEQUENCE: 33

```
Asn Arg Ile Val Gln Gln Arg Thr Ser Ser Arg
1               5                   10
```

<210> SEQ ID NO 34
<211> LENGTH: 11
<212> TYPE: PRT
<213> ORGANISM: Artificial Sequence
<220> FEATURE:
<223> OTHER INFORMATION: peptide (203)

<400> SEQUENCE: 34

```
Arg Arg Ile Val Lys Leu Arg Trp Phe Lys Arg
1               5                   10
```

<210> SEQ ID NO 35
<211> LENGTH: 12
<212> TYPE: PRT
<213> ORGANISM: Artificial Sequence
<220> FEATURE:
<223> OTHER INFORMATION: peptide (204)

<400> SEQUENCE: 35

```
Arg Arg Leu Ile Trp Arg Arg Phe Lys Trp Leu Arg
1               5                   10
```

<210> SEQ ID NO 36
<211> LENGTH: 11
<212> TYPE: PRT
<213> ORGANISM: Artificial Sequence
<220> FEATURE:
<223> OTHER INFORMATION: peptide (205)

<400> SEQUENCE: 36

```
Lys Arg Ile Val Arg Trp Arg Thr Arg Lys Arg
1               5                   10
```

<210> SEQ ID NO 37
<211> LENGTH: 11
<212> TYPE: PRT
<213> ORGANISM: Artificial Sequence
<220> FEATURE:
<223> OTHER INFORMATION: peptide (206)

<400> SEQUENCE: 37

```
Lys Arg Ile Val Arg Trp Arg Trp Arg Lys Arg
1               5                   10
```

<210> SEQ ID NO 38
<211> LENGTH: 12
<212> TYPE: PRT
<213> ORGANISM: Artificial Sequence
<220> FEATURE:
<223> OTHER INFORMATION: peptide (207)

<400> SEQUENCE: 38

```
Lys Arg Ile Val Arg Trp Arg Lys Leu Lys Arg Lys
1               5                   10
```

<210> SEQ ID NO 39
<211> LENGTH: 11
<212> TYPE: PRT
<213> ORGANISM: Artificial Sequence
<220> FEATURE:
<223> OTHER INFORMATION: peptide (208)

<400> SEQUENCE: 39

```
Trp Arg Ile Leu Arg Trp Arg Lys Leu Lys Arg
1               5                   10
```

<210> SEQ ID NO 40
<211> LENGTH: 11
<212> TYPE: PRT
<213> ORGANISM: Artificial Sequence
<220> FEATURE:
<223> OTHER INFORMATION: peptide (209)

<400> SEQUENCE: 40

```
Trp Arg Ile Val Arg Trp Arg Lys Leu Lys Arg
1               5                   10
```

<210> SEQ ID NO 41
<211> LENGTH: 11
<212> TYPE: PRT
<213> ORGANISM: Artificial Sequence
<220> FEATURE:
<223> OTHER INFORMATION: peptide (210)

<400> SEQUENCE: 41

```
Trp Arg Ile Val Gln Trp Arg Lys Leu Lys Arg
1               5                   10
```

<210> SEQ ID NO 42
<211> LENGTH: 11
<212> TYPE: PRT
<213> ORGANISM: Artificial Sequence
<220> FEATURE:
<223> OTHER INFORMATION: peptide (211)

<400> SEQUENCE: 42

```
Lys Arg Ile Val Arg Arg Arg Thr Phe Lys Arg
1               5                   10
```

<210> SEQ ID NO 43
<211> LENGTH: 11
<212> TYPE: PRT
<213> ORGANISM: Artificial Sequence
<220> FEATURE:
<223> OTHER INFORMATION: peptide (212)

<400> SEQUENCE: 43

```
Lys Arg Trp Arg Lys Trp Arg Leu Phe Lys Arg
1               5                   10
```

<210> SEQ ID NO 44
<211> LENGTH: 11
<212> TYPE: PRT
<213> ORGANISM: Artificial Sequence
<220> FEATURE:
<223> OTHER INFORMATION: Chain (213)

<400> SEQUENCE: 44

```
Asn Arg Ile Val Leu Leu Arg Thr Phe Lys Arg
```

```
1               5                   10
```

<210> SEQ ID NO 45
<211> LENGTH: 11
<212> TYPE: PRT
<213> ORGANISM: Artificial Sequence
<220> FEATURE:
<223> OTHER INFORMATION: peptide (214)

<400> SEQUENCE: 45

```
Asn Arg Ile Val Lys Lys Arg Thr Phe Lys Arg
1               5                   10
```

<210> SEQ ID NO 46
<211> LENGTH: 11
<212> TYPE: PRT
<213> ORGANISM: Artificial Sequence
<220> FEATURE:
<223> OTHER INFORMATION: peptide (215)

<400> SEQUENCE: 46

```
Arg Lys Ile Val Lys Arg Arg Thr Phe Lys Arg
1               5                   10
```

<210> SEQ ID NO 47
<211> LENGTH: 11
<212> TYPE: PRT
<213> ORGANISM: Artificial Sequence
<220> FEATURE:
<223> OTHER INFORMATION: peptide (216)

<400> SEQUENCE: 47

```
Arg Lys Ile Val Trp Trp Arg Thr Phe Lys Arg
1               5                   10
```

<210> SEQ ID NO 48
<211> LENGTH: 11
<212> TYPE: PRT
<213> ORGANISM: Artificial Sequence
<220> FEATURE:
<223> OTHER INFORMATION: peptide (217)

<400> SEQUENCE: 48

```
Arg Leu Ile Val Arg Arg Arg Thr Phe Lys Arg
1               5                   10
```

<210> SEQ ID NO 49
<211> LENGTH: 11
<212> TYPE: PRT
<213> ORGANISM: Artificial Sequence
<220> FEATURE:
<223> OTHER INFORMATION: peeptide (218)

<400> SEQUENCE: 49

```
Arg Arg Ile Val Arg Lys Lys Thr Phe Lys Arg
1               5                   10
```

<210> SEQ ID NO 50
<211> LENGTH: 11
<212> TYPE: PRT
<213> ORGANISM: Artificial Sequence
<220> FEATURE:
<223> OTHER INFORMATION: peptide (219)

<400> SEQUENCE: 50

```
Arg Arg Ile Val Trp Arg Arg Thr Phe Lys Arg
1               5                   10
```

<210> SEQ ID NO 51
<211> LENGTH: 11
<212> TYPE: PRT
<213> ORGANISM: Artificial Sequence
<220> FEATURE:
<223> OTHER INFORMATION: peptide (220)

<400> SEQUENCE: 51

Arg Trp Ile Val Gln Arg Arg Thr Phe Lys Arg
1               5                   10

<210> SEQ ID NO 52
<211> LENGTH: 11
<212> TYPE: PRT
<213> ORGANISM: Artificial Sequence
<220> FEATURE:
<223> OTHER INFORMATION: peptide (221)

<400> SEQUENCE: 52

Arg Val Ile Val Arg Arg Arg Thr Phe Lys Arg
1               5                   10

<210> SEQ ID NO 53
<211> LENGTH: 11
<212> TYPE: PRT
<213> ORGANISM: Artificial Sequence
<220> FEATURE:
<223> OTHER INFORMATION: peptide (222)

<400> SEQUENCE: 53

Trp Lys Ile Val Lys Lys Arg Thr Arg Arg Arg
1               5                   10

<210> SEQ ID NO 54
<211> LENGTH: 11
<212> TYPE: PRT
<213> ORGANISM: Artificial Sequence
<220> FEATURE:
<223> OTHER INFORMATION: peptide (223)

<400> SEQUENCE: 54

Trp Arg Ile Val Arg Arg Arg Thr Phe Lys Arg
1               5                   10

<210> SEQ ID NO 55
<211> LENGTH: 11
<212> TYPE: PRT
<213> ORGANISM: Artificial Sequence
<220> FEATURE:
<223> OTHER INFORMATION: peptide (301)

<400> SEQUENCE: 55

Ile Ile Lys Arg Phe Arg Leu Phe Lys Lys Leu
1               5                   10

<210> SEQ ID NO 56
<211> LENGTH: 11
<212> TYPE: PRT
<213> ORGANISM: Artificial Sequence
<220> FEATURE:
<223> OTHER INFORMATION: peptide (302)

<400> SEQUENCE: 56

Ile Leu Lys Arg Trp Trp Leu Phe Lys Lys Leu
1               5                   10

```
<210> SEQ ID NO 57
<211> LENGTH: 11
<212> TYPE: PRT
<213> ORGANISM: Artificial Sequence
<220> FEATURE:
<223> OTHER INFORMATION: peptide (303)

<400> SEQUENCE: 57

Ile Trp Lys Arg Phe Arg Leu Phe Lys Lys Arg
1               5                   10

<210> SEQ ID NO 58
<211> LENGTH: 11
<212> TYPE: PRT
<213> ORGANISM: Artificial Sequence
<220> FEATURE:
<223> OTHER INFORMATION: peptide (304)

<400> SEQUENCE: 58

Ile Trp Lys Arg Phe Arg Leu Phe Lys Lys Trp
1               5                   10

<210> SEQ ID NO 59
<211> LENGTH: 11
<212> TYPE: PRT
<213> ORGANISM: Artificial Sequence
<220> FEATURE:
<223> OTHER INFORMATION: peptide (305)

<400> SEQUENCE: 59

Arg Leu Lys Trp Phe Trp Leu Arg Lys Leu Lys
1               5                   10

<210> SEQ ID NO 60
<211> LENGTH: 11
<212> TYPE: PRT
<213> ORGANISM: Artificial Sequence
<220> FEATURE:
<223> OTHER INFORMATION: peptide (306)

<400> SEQUENCE: 60

Arg Leu Lys Arg Trp Arg Leu Phe Arg Lys Arg
1               5                   10

<210> SEQ ID NO 61
<211> LENGTH: 11
<212> TYPE: PRT
<213> ORGANISM: Artificial Sequence
<220> FEATURE:
<223> OTHER INFORMATION: peptide (307)

<400> SEQUENCE: 61

Arg Leu Lys Trp Phe Trp Leu Phe Arg Lys Arg
1               5                   10

<210> SEQ ID NO 62
<211> LENGTH: 11
<212> TYPE: PRT
<213> ORGANISM: Artificial Sequence
<220> FEATURE:
<223> OTHER INFORMATION: peptide (308)

<400> SEQUENCE: 62

Arg Leu Lys Trp Phe Leu Leu Phe Arg Lys Arg
1               5                   10
```

<210> SEQ ID NO 63
<211> LENGTH: 11
<212> TYPE: PRT
<213> ORGANISM: Artificial Sequence
<220> FEATURE:
<223> OTHER INFORMATION: peptide (309)

<400> SEQUENCE: 63

Trp Arg Lys Trp Phe Trp Leu Phe Lys Lys Arg
1               5                   10

<210> SEQ ID NO 64
<211> LENGTH: 11
<212> TYPE: PRT
<213> ORGANISM: Artificial Sequence
<220> FEATURE:
<223> OTHER INFORMATION: peptide (310)

<400> SEQUENCE: 64

Lys Arg Lys Trp Arg Trp Leu Phe Lys Lys Leu
1               5                   10

<210> SEQ ID NO 65
<211> LENGTH: 11
<212> TYPE: PRT
<213> ORGANISM: Artificial Sequence
<220> FEATURE:
<223> OTHER INFORMATION: peptide (311)

<400> SEQUENCE: 65

Lys Leu Lys Trp Phe Trp Leu Phe Lys Lys Arg
1               5                   10

<210> SEQ ID NO 66
<211> LENGTH: 11
<212> TYPE: PRT
<213> ORGANISM: Artificial Sequence
<220> FEATURE:
<223> OTHER INFORMATION: peptide (312)

<400> SEQUENCE: 66

Lys Leu Lys Lys Phe Lys Leu Phe Lys Lys Arg
1               5                   10

<210> SEQ ID NO 67
<211> LENGTH: 12
<212> TYPE: PRT
<213> ORGANISM: Artificial Sequence
<220> FEATURE:
<223> OTHER INFORMATION: peptide (313)

<400> SEQUENCE: 67

Arg Leu Lys Arg Phe Arg Leu Phe Arg Lys Arg Lys
1               5                   10

<210> SEQ ID NO 68
<211> LENGTH: 11
<212> TYPE: PRT
<213> ORGANISM: Artificial Sequence
<220> FEATURE:
<223> OTHER INFORMATION: peptide (314)

<400> SEQUENCE: 68

Lys Arg Lys Arg Phe Arg Leu Phe Lys Lys Arg
1               5                   10

<210> SEQ ID NO 69

<211> LENGTH: 11
<212> TYPE: PRT
<213> ORGANISM: Artificial Sequence
<220> FEATURE:
<223> OTHER INFORMATION: peptide (315)

<400> SEQUENCE: 69

Arg Leu Lys Arg Phe Arg Leu Phe Lys Lys Leu
1               5                   10

<210> SEQ ID NO 70
<211> LENGTH: 11
<212> TYPE: PRT
<213> ORGANISM: Artificial Sequence
<220> FEATURE:
<223> OTHER INFORMATION: peptide (316)

<400> SEQUENCE: 70

Arg Arg Lys Arg Phe Arg Leu Phe Lys Lys Met
1               5                   10

<210> SEQ ID NO 71
<211> LENGTH: 11
<212> TYPE: PRT
<213> ORGANISM: Artificial Sequence
<220> FEATURE:
<223> OTHER INFORMATION: peptide (317)

<400> SEQUENCE: 71

Arg Arg Lys Arg Phe Arg Leu Phe Arg Arg Lys
1               5                   10

<210> SEQ ID NO 72
<211> LENGTH: 11
<212> TYPE: PRT
<213> ORGANISM: Artificial Sequence
<220> FEATURE:
<223> OTHER INFORMATION: peptide (318)

<400> SEQUENCE: 72

Arg Trp Lys Arg Phe Arg Leu Phe Lys Lys Arg
1               5                   10

<210> SEQ ID NO 73
<211> LENGTH: 11
<212> TYPE: PRT
<213> ORGANISM: Artificial Sequence
<220> FEATURE:
<223> OTHER INFORMATION: peptide (319)

<400> SEQUENCE: 73

Arg Trp Lys Arg Phe Arg Leu Phe Lys Lys Trp
1               5                   10

<210> SEQ ID NO 74
<211> LENGTH: 11
<212> TYPE: PRT
<213> ORGANISM: Artificial Sequence
<220> FEATURE:
<223> OTHER INFORMATION: peptide (320)

<400> SEQUENCE: 74

Trp Lys Lys Gly Phe Gly Leu Phe Lys Lys Met
1               5                   10

<210> SEQ ID NO 75
<211> LENGTH: 11

```
<212> TYPE: PRT
<213> ORGANISM: Artificial Sequence
<220> FEATURE:
<223> OTHER INFORMATION: paptide (321)

<400> SEQUENCE: 75

Trp Lys Lys Arg Phe Arg Leu Phe Lys Lys Leu
1               5                   10

<210> SEQ ID NO 76
<211> LENGTH: 11
<212> TYPE: PRT
<213> ORGANISM: Artificial Sequence
<220> FEATURE:
<223> OTHER INFORMATION: peptide (322)

<400> SEQUENCE: 76

Trp Leu Arg Arg Phe Arg Leu Phe Arg Arg Leu
1               5                   10

<210> SEQ ID NO 77
<211> LENGTH: 12
<212> TYPE: PRT
<213> ORGANISM: Artificial Sequence
<220> FEATURE:
<223> OTHER INFORMATION: peptide (323)

<400> SEQUENCE: 77

Arg Leu Lys Arg Phe Leu Leu Phe Arg Lys Arg Leu
1               5                   10

<210> SEQ ID NO 78
<211> LENGTH: 11
<212> TYPE: PRT
<213> ORGANISM: Artificial Sequence
<220> FEATURE:
<223> OTHER INFORMATION: peptide (324)

<400> SEQUENCE: 78

Lys Arg Lys Trp Phe Trp Leu Phe Lys Lys Leu
1               5                   10

<210> SEQ ID NO 79
<211> LENGTH: 11
<212> TYPE: PRT
<213> ORGANISM: Artificial Sequence
<220> FEATURE:
<223> OTHER INFORMATION: peptide (325)

<400> SEQUENCE: 79

Lys Leu Lys Arg Phe Arg Leu Phe Lys Lys Arg
1               5                   10

<210> SEQ ID NO 80
<211> LENGTH: 8
<212> TYPE: PRT
<213> ORGANISM: Artificial Sequence
<220> FEATURE:
<223> OTHER INFORMATION: peptide (326)

<400> SEQUENCE: 80

Met His His His His His His Met
1               5
```

ANTIMICROBIAL PEPTIDES, THEIR VARIANTS AND USES

PRIORITY

This application is a U.S national application of the international application number PCT/FI2016/050483 filed on Jun. 29, 2016 and claiming priority of Finnish national application FI2015517 filed on Jun. 30, 2015, the contents of both of which are incorporated herein by reference.

SEQUENCE LISTING

This application contains sequence listing provided on a written format and as computer readable format which is identical to the written format and is incorporated by reference in its entirety.

Sequence Listing with the specific file name Updated_sequence_listing_to_Patent_Office_PI100446.txt, having a particular size of 20.7 kb, submitted to the PTO on Jun. 12, 2019, is hereby incorporated by reference in its full entirety and in toto.

FIELD OF INVENTION

The present invention relates to antimicrobial peptides or variants thereof, to a method of killing or inhibiting growth of microbes and to a use of the peptide described here as a medicament, feed additive, preservative or surfactant.

BACKGROUND

Among drug compounds, antibiotics have had a tremendous impact on the life expectancy of mankind. However, the capacity of microbes to develop resistance is almost unlimited. Multi-drug resistance has become a very common and dangerous characteristic of many human pathogens, and drug resistance is spreading across the globe.

Endophytes are promising producers of a wide array of secondary metabolites with potential application in biomedicine, pharmaceutical and healthcare industries. The methodology typically used for studying functional diversity of endophytes is based on isolation with an emphasis towards fast-growing strains, thus not representing the full biodiversity. Methods such as denaturing gradient gel electrophoresis (DGGE), restriction fragment length polymorphism (RFLP) or cloning and direct sequencing are used for analyzing the diversity of unculturable fungal communities in plants, but such methods are not suitable for the functional studies. A frequent problem with endophytes is that they produce metabolites only for a certain period of time in vitro and then become inactive, lose viability or ability to produce bioactive secondary metabolites. Such culturing problems on other microbes have earlier been one of the driving forces for development of new methods to access the vast microbial wealth.

Antimicrobial peptides (AMPs) are evolutionarily conserved and produced by innate immune system in all complex organisms. They serve as the first line of defense in humans and mammals. AMPs are polypeptides composed of 10-50 amino acids with ≥30% of hydrophobic ratios and positive charge. In general, AMPs have broadspectrum antimicrobial activity against bacteria, fungi and yeast. WO 2011/113999 discloses tryptic polypeptides from endophyte of *Empetrum nigrum* and methods for obtaining them. Based on in silico analysis the peptides are predicted to have antimicrobial activity.

There is an urgent need for new molecules having activity against various pathogenic microbes. This invention meets these needs as explained in the following.

SUMMARY OF THE INVENTION

Crowberry (*Empetrum nigrum*) is a perennial shrub growing in the northern hemisphere that has traditionally been used for treating infectious diseases and was considered a good candidate for such studies. The present invention provides novel antimicrobial (poly) peptides derived from an endophyte of *E. nigrum* and variants thereof having improved activity against various microbes.

The first aspect of the invention is to provide an antimicrobial peptide or a variant thereof. According to the invention said polypeptide comprises SEQ ID NO: 5 or has at least 37% identity to SEQ ID NO: 5.

The second aspect of the invention is a method of killing or inhibiting growth of microbes. According to the invention said method comprises a step of treating said microbes with a peptide or a variant thereof here described.

The third aspect of the invention is a use of the peptide or a variant thereof here described as a medicament, feed additive, preservative or surfactant.

Considerable advantages are obtained by the invention. The AMPs are known to be active against broad spectrum of microbes, including fungi and both Gram positive and Gram negative bacteria. Small AMPs are easy to synthesize and commercially viable as the cost of production is minimal. AMPs are not known to develop resistance in bacteria. The present invention relates to novel antimicrobial peptides, their variants and use in various applications.

BRIEF DESCRIPTION OF THE DRAWINGS

FIG. 1. An agar-overlay assay showing subclones with antibacterial activity (a) and subclones without activity (s) towards *S. aureus*, identified in the *E. coli*-based endophytic metagenomic library.

FIG. 2. Predicted amino acid sequence of *Empetrum nigrum* metagenomic antibacterial protein 1. The predicted protein has 549 residues. Highly conserved PPR-sequences (pentatricopeptide repeats) are underlined.

FIG. 4a shows an alignment of 25 variants of "Met10"-peptide (Chain 100) defined by SEQ ID NO: 4.

FIG. 4b shows an alignment of 23 variants of "Met11"-peptide (Chain 200) defined by SEQ ID NO: 5.

FIG. 4c shows an alignment of 25 variants of "Met12"-peptide (Chain 300) defined by SEQ ID NO: 6.

FIG. 5a shows an alignment of 9 variants of "Met10"-peptide (Chain 100) defined by SEQ ID NO: 4.

FIG. 5b shows an alignment of 10 variants of "Met11"-peptide (Chain 200) defined by SEQ ID NO: 5.

FIG. 5c shows an alignment of 13 variants of "Met12"-peptide (Chain 300) defined by SEQ ID NO: 6.

Figure 6A:
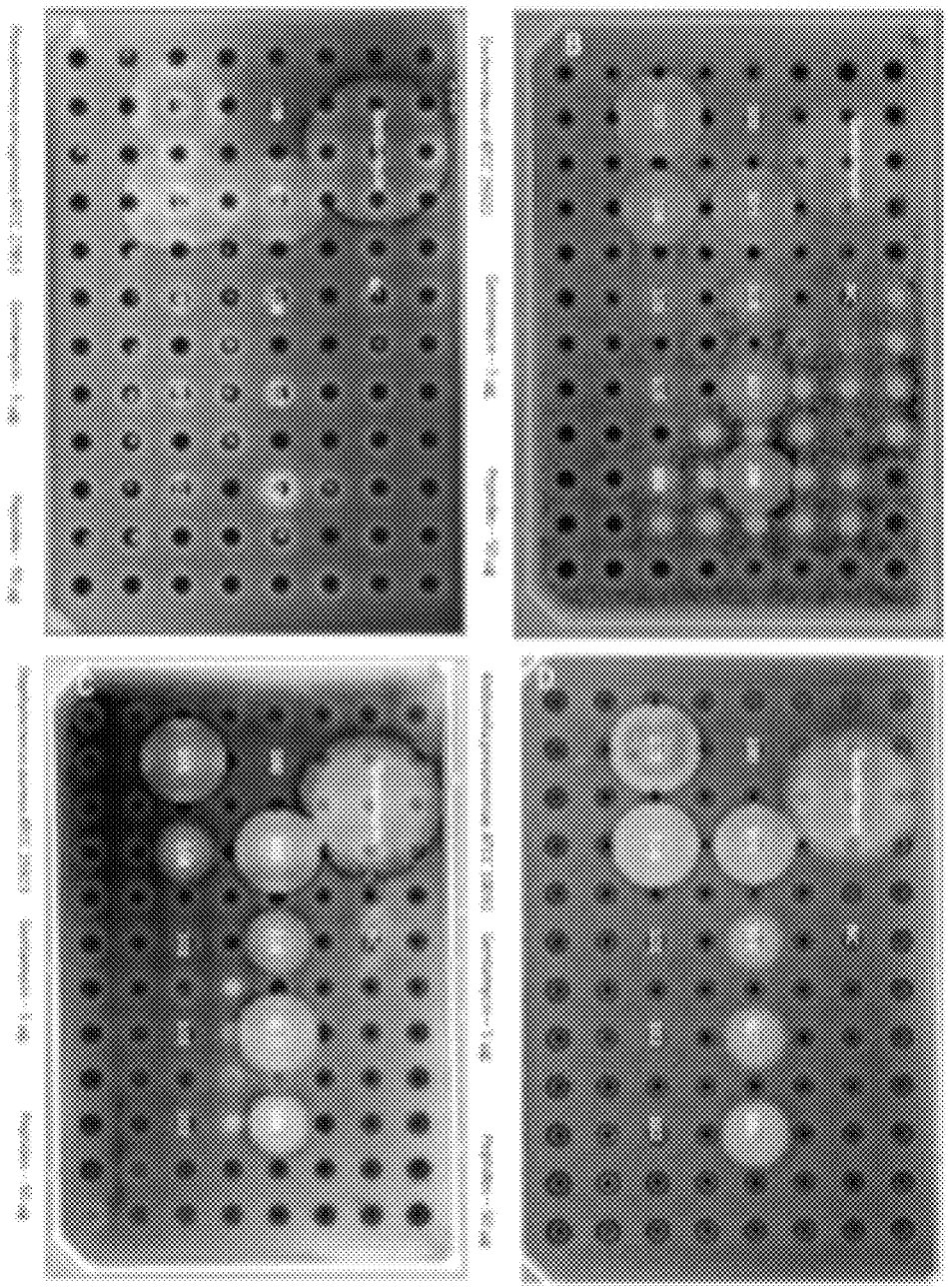
FIG. 6a. Radial Diffusion assay (RDA) of synthesized peptide variants Chain 100-109, 50 µg each, tested against *Escherichia coli* (ATCC 25922), *Staphylococcus aureus* (ATCC 25923), *Klebsiella pneumoniae* (ATCC 10031) and *Pseudomonas aeruginosa* (ATCC 27853), NC=negative control, Gentamicin 5 µg FIG. 6b. Radial Diffusion assay (RDA) of synthesized peptide variants Chain 200-210, 50 µg each, tested against
Figure 6B:
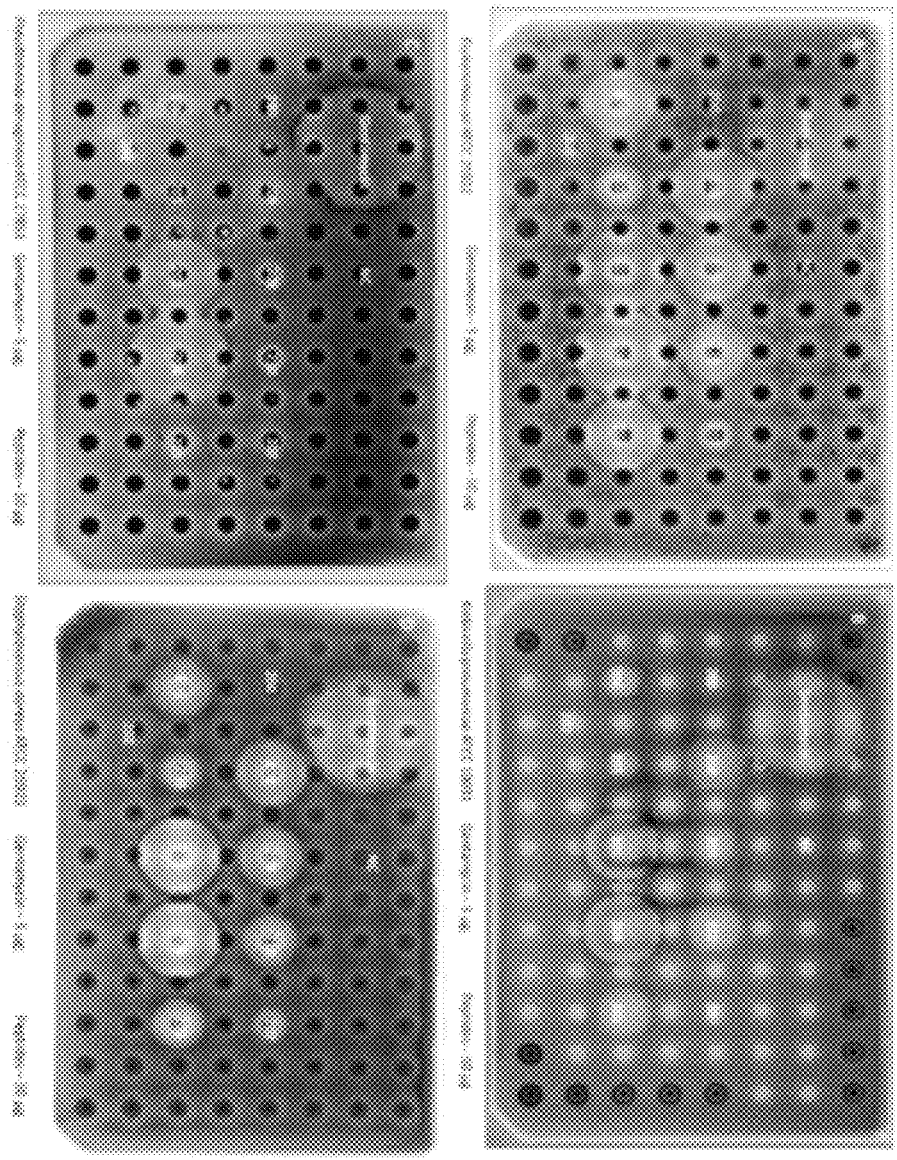
Figure 6C:
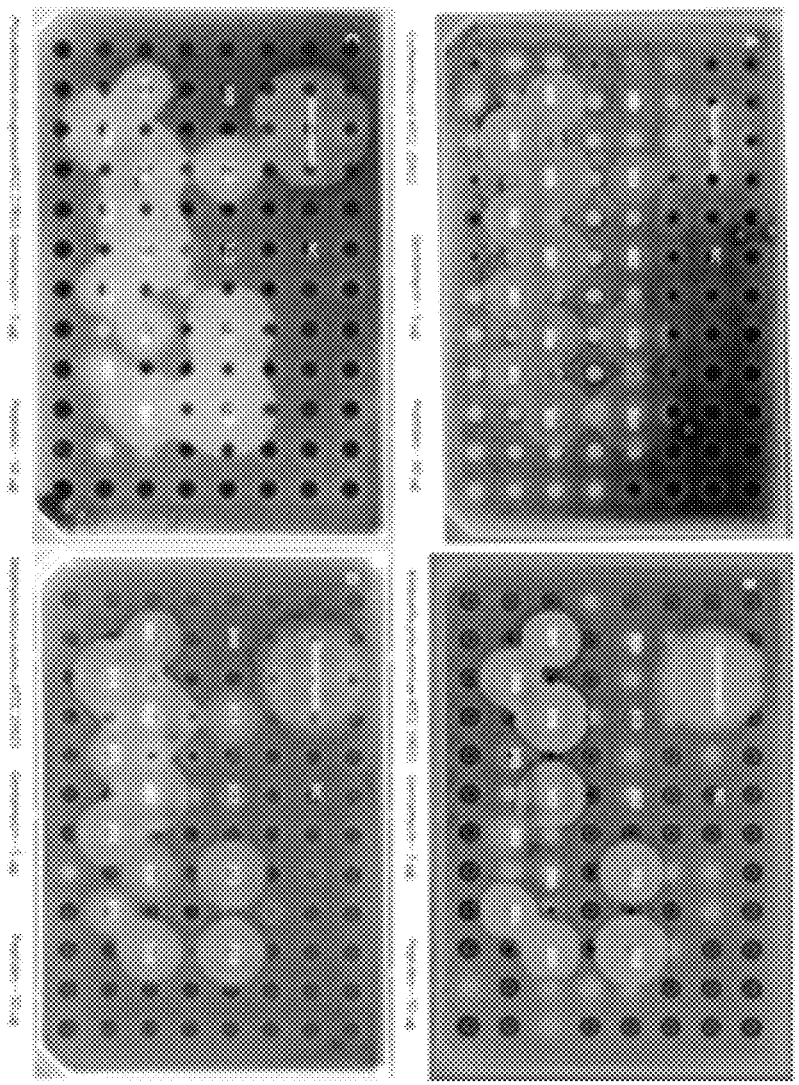
Figure 7A:
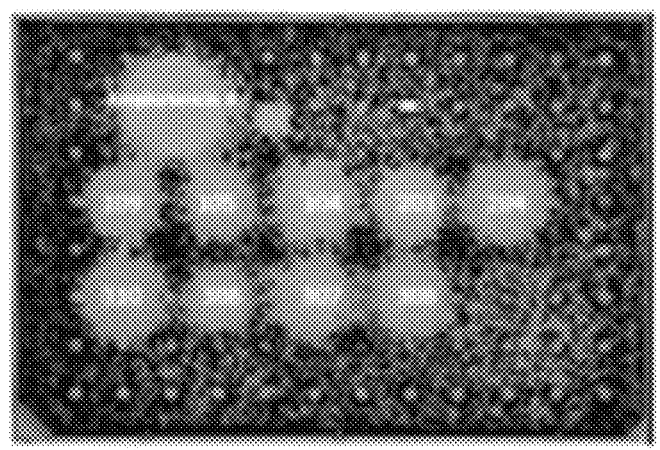

*Escherichia coli* (ATCC 25922), *Staphylococcus aureus* (ATCC 25923), *Klebsiella pneumoniae* (ATCC 10031) and *Pseudomonas aeruginosa* (ATCC 27853), NC=negative control, Gentamicin 5 μg FIG. 6c. Radial Diffusion assay (RDA) of synthesized peptide variants Chains 300-313, 50 μg each, tested against *Escherichia coli* (ATCC 25922), *Staphylococcus aureus* (ATCC 25923), *Klebsiella pneumoniae* (ATCC 10031) and *Pseudomonas aeruginosa* (ATCC 27853), NC=negative control, Gentamicin 5 μg FIG. 7a. Radial Diffusion assay (RDA) of synthesized peptide variants Chains 109, 105, 104, 201, 204, 310, 308, 307 and 306, 20 μg each, tested against *Aspergillus flavus* (DSM 1959), NC=negative control, Amphotericin B 20 μg.

Figure 7B:
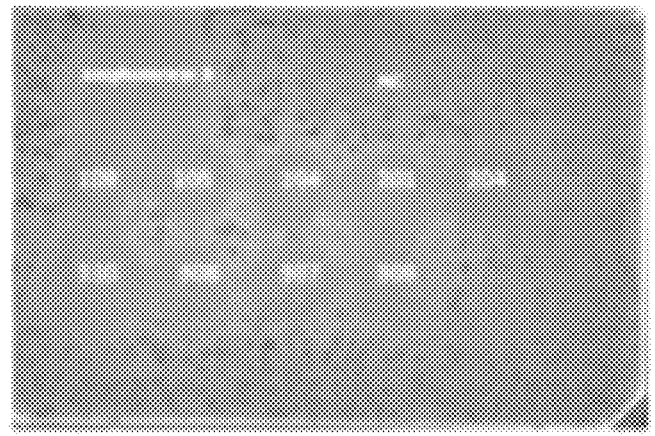

FIG. 7b. Radial Diffusion assay (RDA) of synthesized peptide variants chains 109, 105, 104, 201, 204, 310, 308, 307 and 306, 20 μg each, tested against *Penicillium chrysogenum* (DSM 1075), NC=negative control, Amphotericin B 20 μg.

Figure 8A:
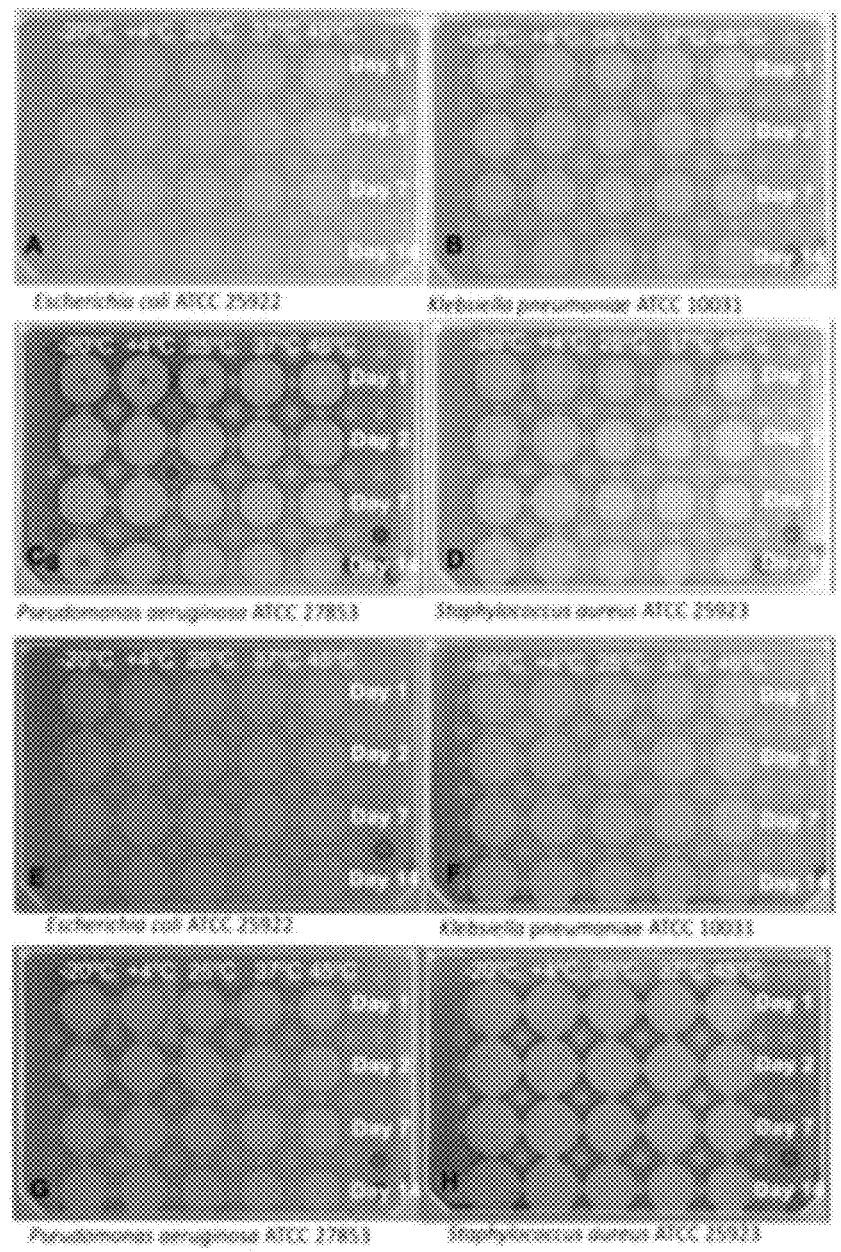

FIG. 8a. Thermostability of the chain peptides 104 (A-D) and 105 (E-H) tested at various temperatures over a period of 14 days by radial diffusion assay. Antibacterial activity was tested by aliquoting 20 μg of peptides incubated at different temperature and activity was measured by zone of inhibition. Peptides at −20° C. served as control.

Figure 8B:
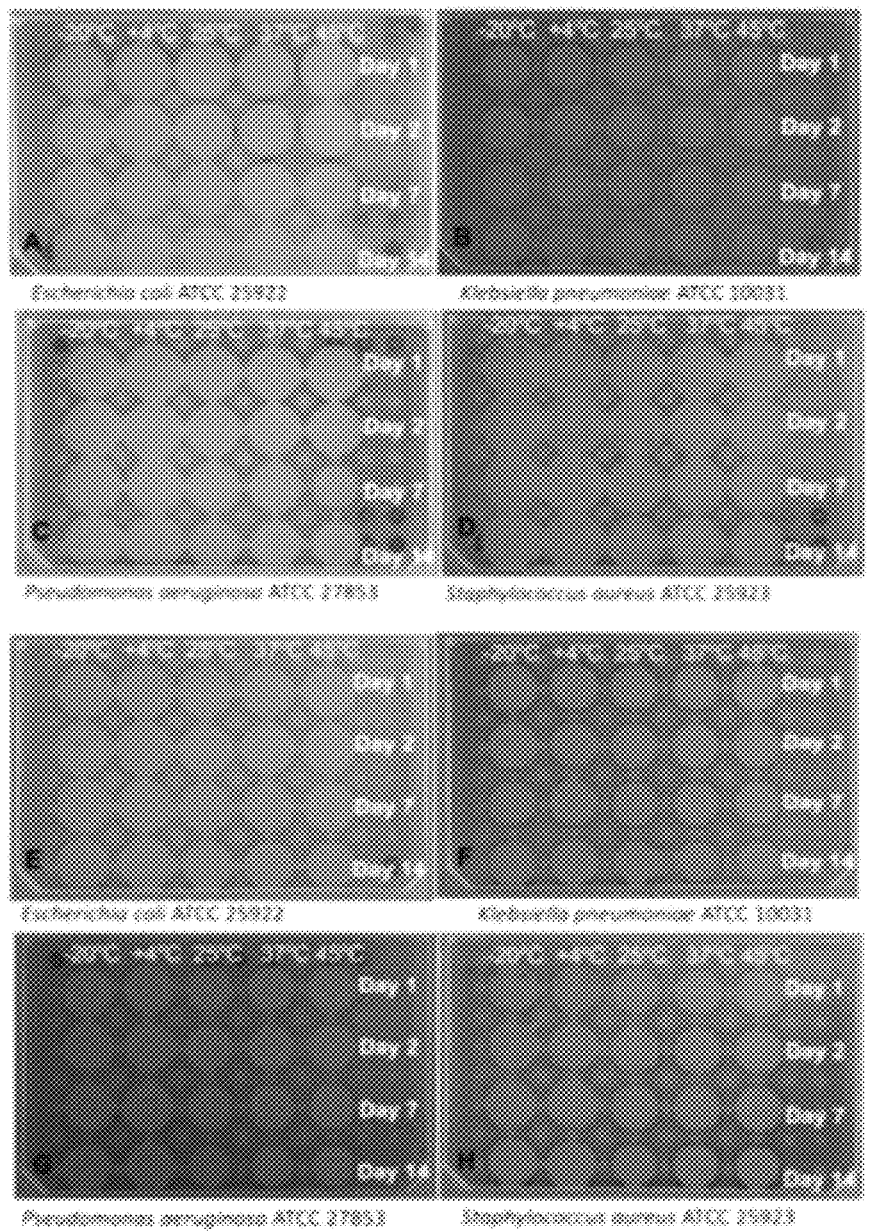

FIG. 8b. Thermostability of the chain peptides 201 (A-D) and 204 (E-H) tested at various temperatures over a period of 14 days by radial diffusion assay. Antibacterial activity was tested by aliquoting 20 μg of peptides incubated at different temperature and activity was measured by zone of inhibition. Peptides at −20° C. served as control.

Figure 8C:
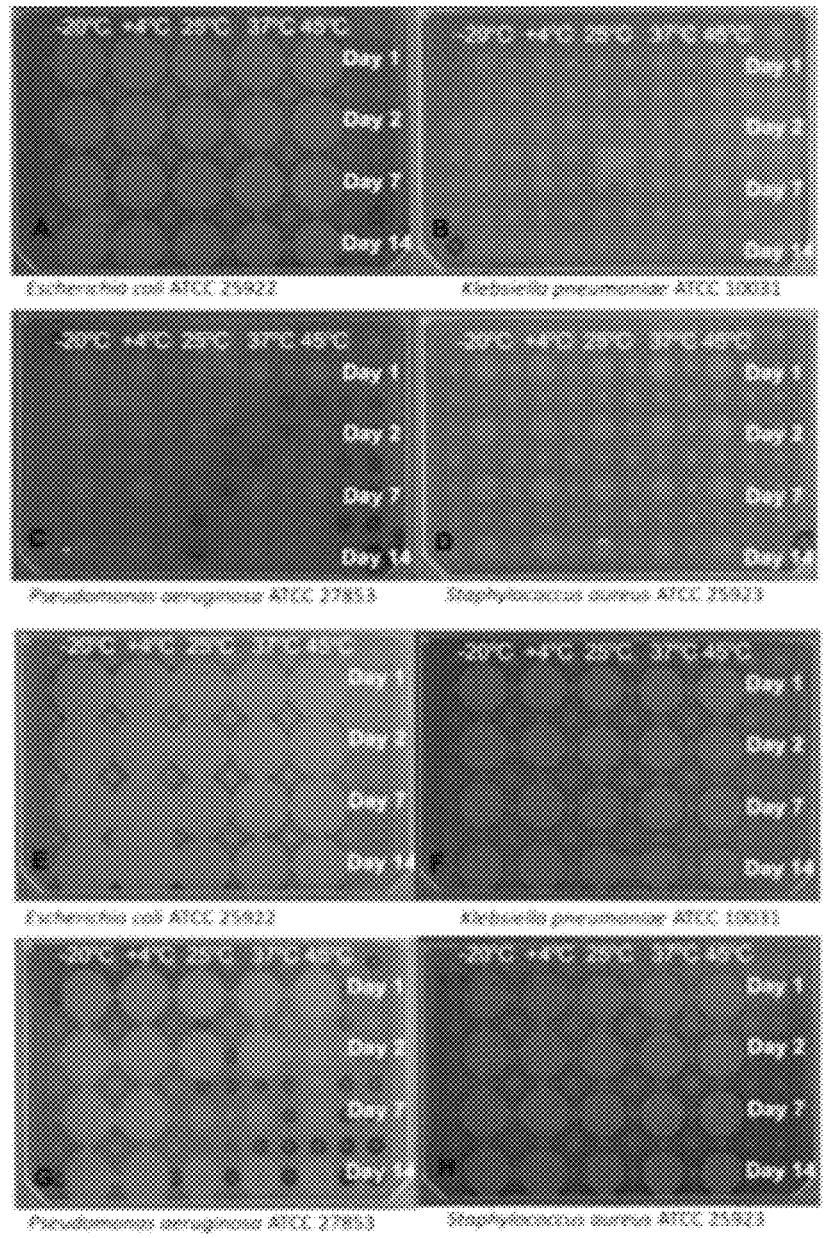

FIG. 8c. Thermostability of the chain peptides 306 (A-D) and 308 (E-H) tested at various temperatures over a period of 14 days by radial diffusion assay. Antibacterial activity was tested by aliquoting 20 μg of peptides incubated at different temperature and activity was measured by zone of inhibition. Peptides at −20° C. served as control.

Figure 9A:
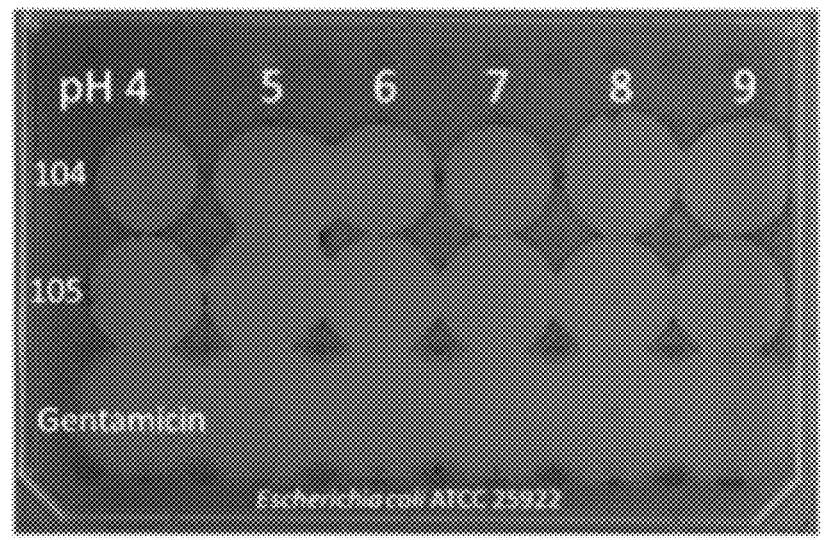

FIG. 9a. pH stability of chain peptides 104 and 105 was determined by radial diffusion assay (RDA). Different pH ranging from 4-9 was used to check the zone of inhibition.

Figure 9B:
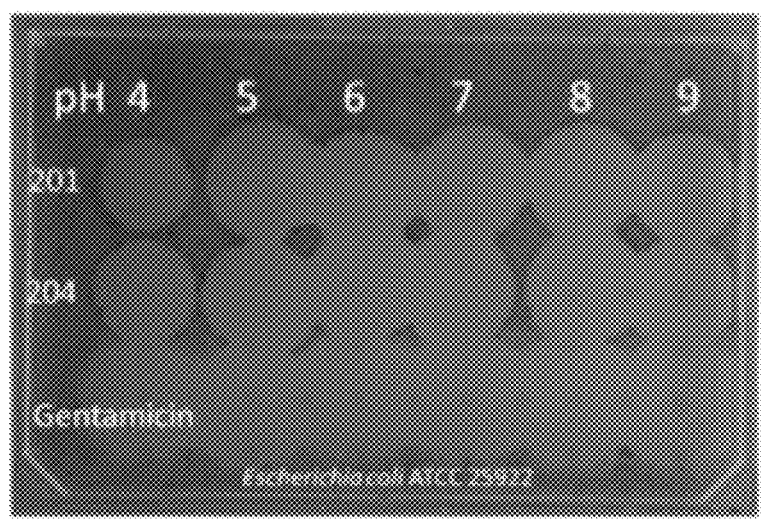

FIG. 9b. pH stability of chain peptides 201 and 204 was determined by radial diffusion assay (RDA). Different pH ranging from 4-9 was used to check the zone of inhibition.

Figure 9C:
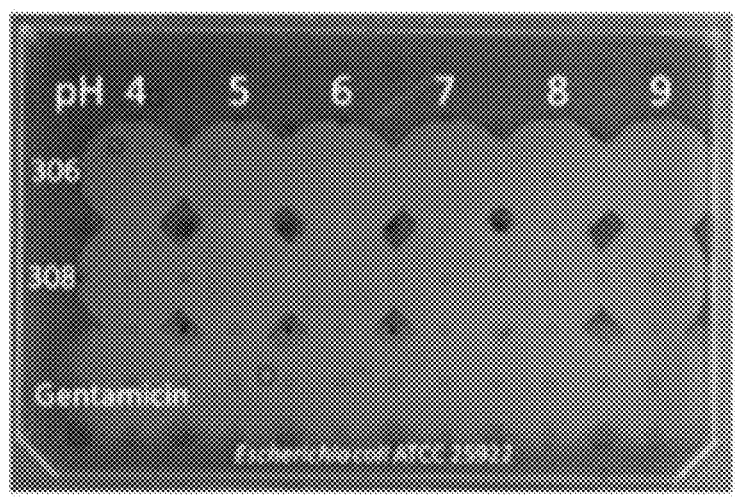

FIG. 9c. pH stability of chain peptides 306 and 308 was determined by radial diffusion assay (RDA). Different pH ranging from 4-9 was used to check the zone of inhibition.

Figure 10:
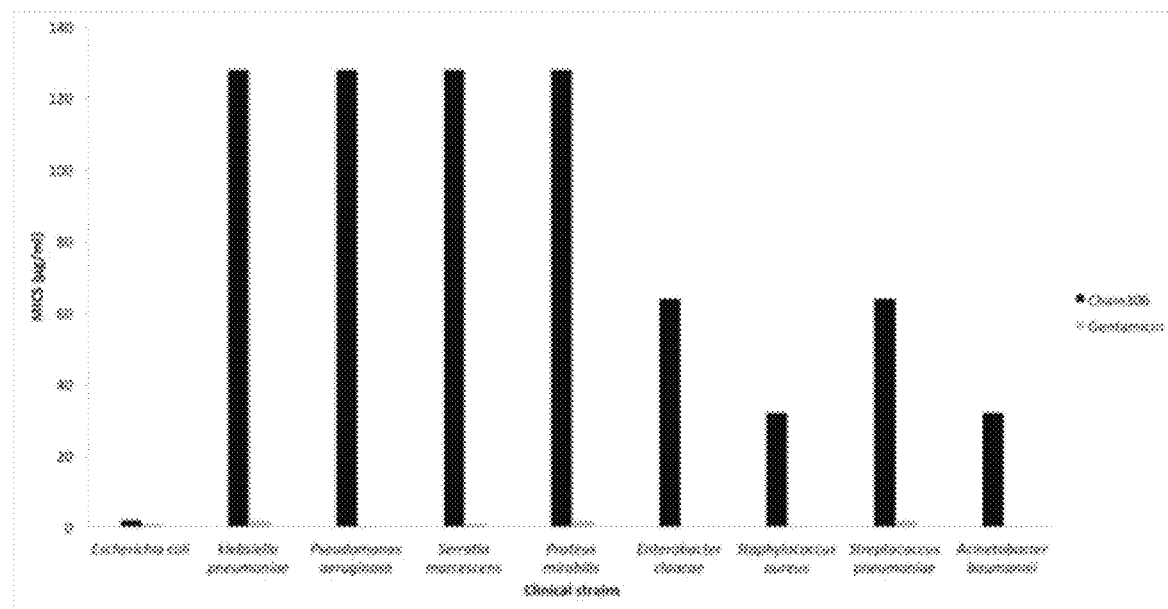

FIG. 10. Narrow spectrum antimicrobial activity of chain peptide 306.

Figure 11A:
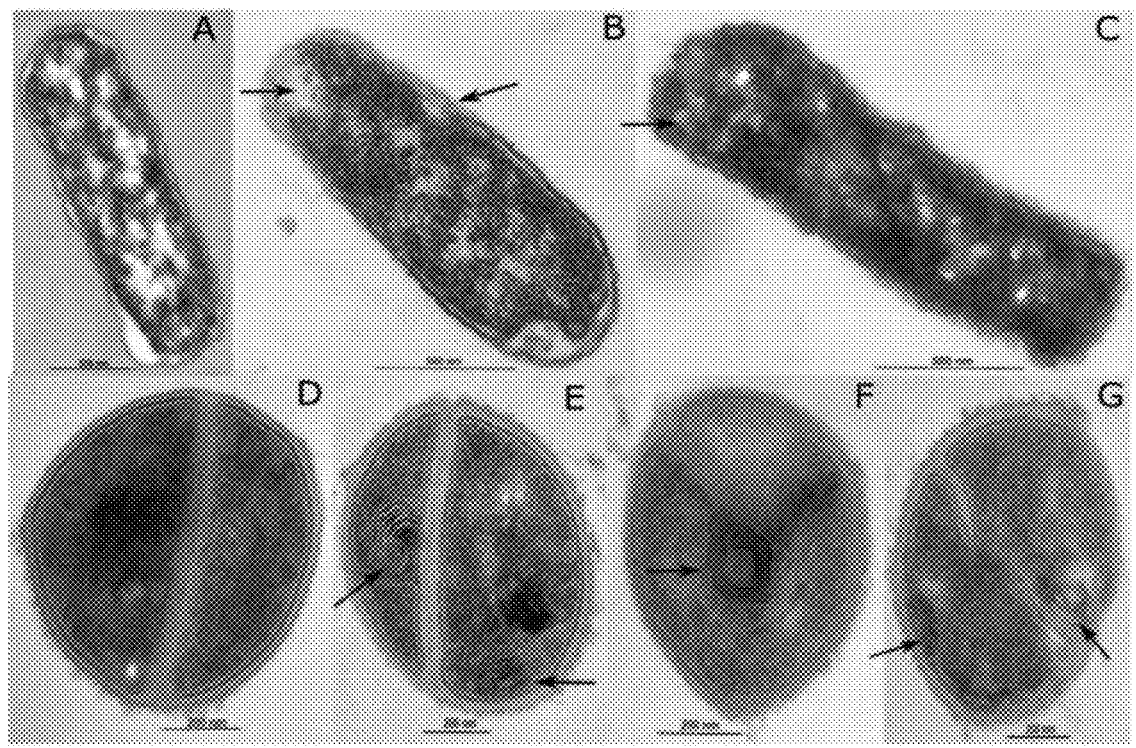

FIG. 11a. Transmission electron microscopy (TEM) image of *E. coli* (A-C) and *S. aureus* (D-G) exposed to 10 μg/ml of chain 105 at 37° C. for 1 h. Control (A & D); Treated with chain 105 (B-C & E-G).

Figure 11B:
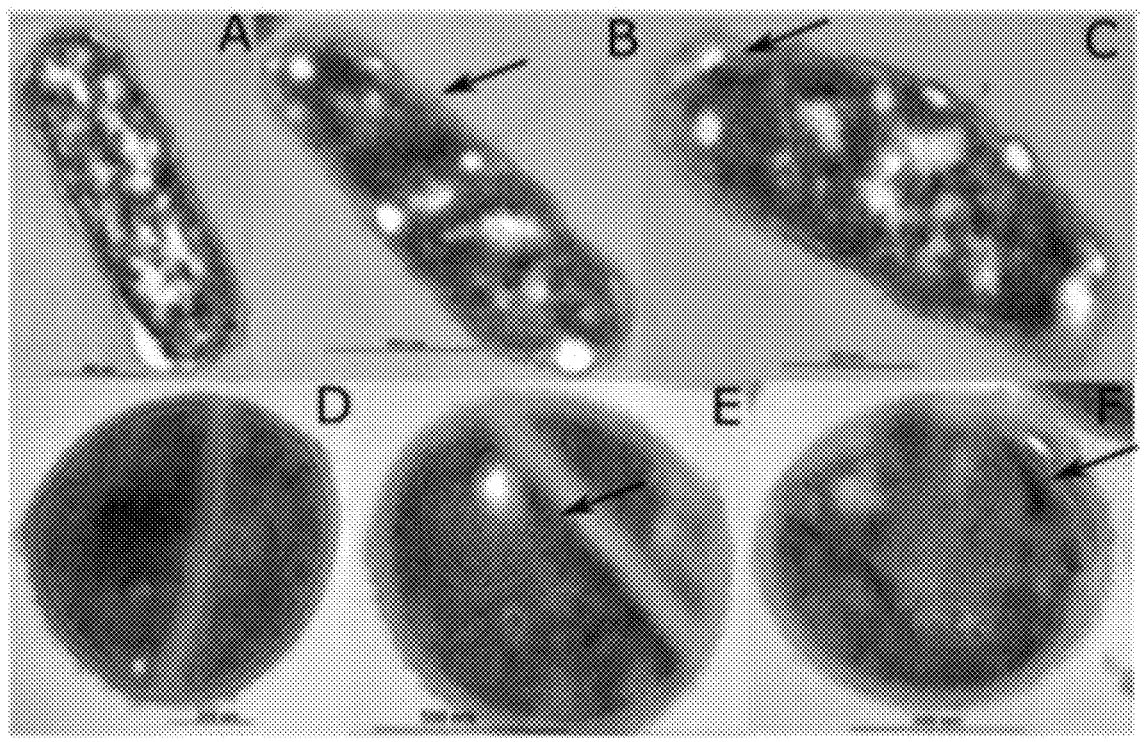

FIG. 11b. Transmission electron microscopy (TEM) image of *E. coli* (A-C) and *S. aureus* (D-F) exposed to 10 μg/ml of chain 201 at 37° C. for 1 h. Control (A & D); Treated with chain 201 (B-C & E-F).

Figure 11C:
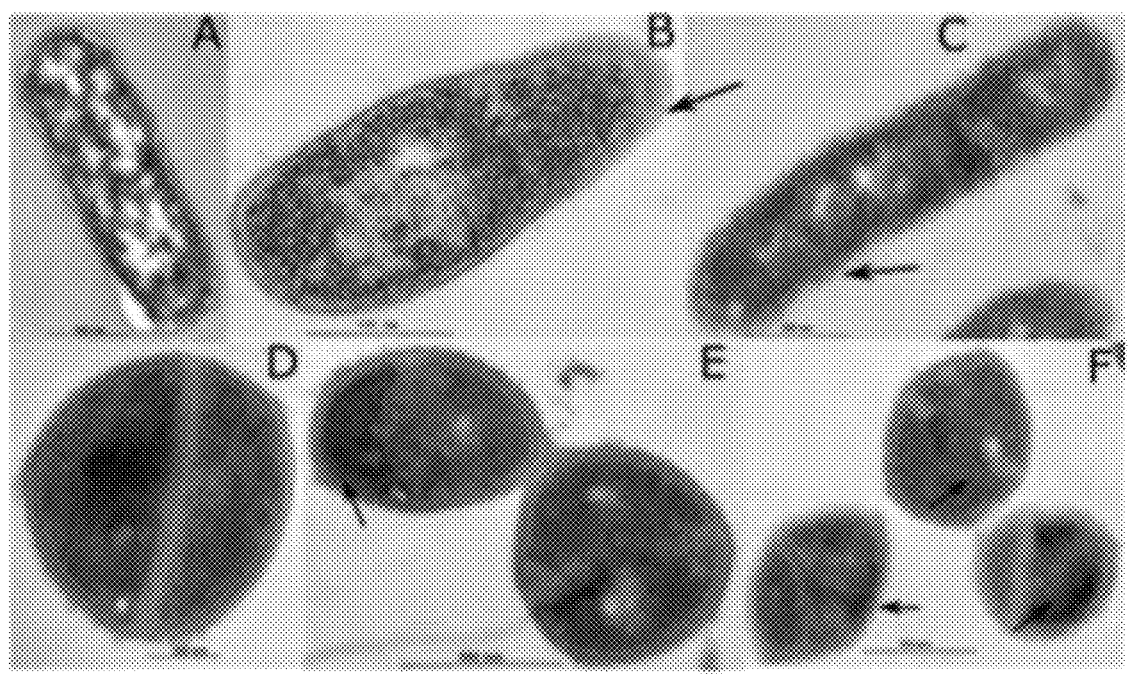

FIG. 11c. Transmission electron microscopy (TEM) image of *E. coli* (A-C) and *S. aureus* (D-F) exposed to 10 μg/ml of chain 308 at 37° C. for 1 h. Control (A & D); Treated with chain 308 (B-C & E-F).

Figure 12:
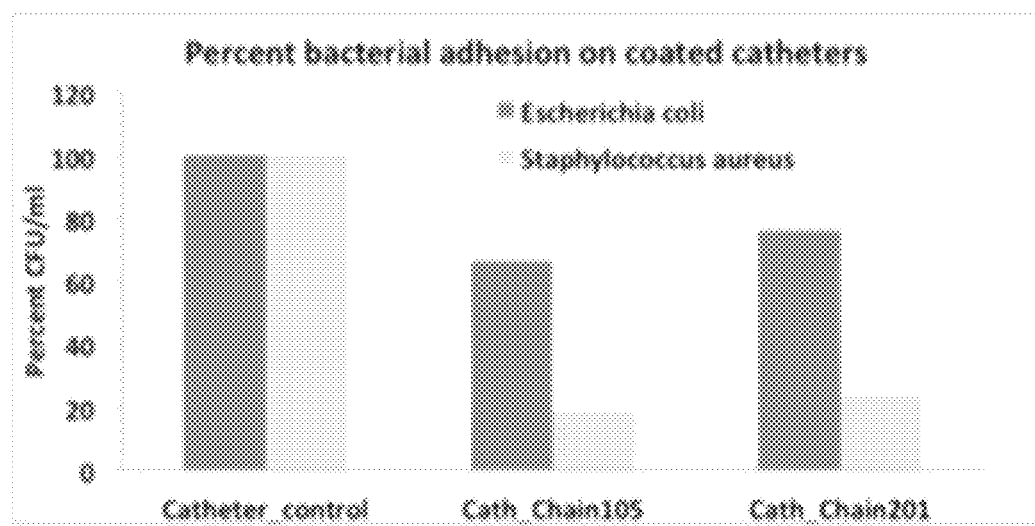

FIG. 12. Antibacterial activity of Chain 105 and 201 immobilized catheters. Silicon catheters were used as controls.

DETAILED DESCRIPTION

Endophytes, microorganisms which spend their entire life cycle, or parts of it, inside of healthy tissues of a host plant, are found in all plant species. Whereas the majority of endophytes cannot be cultured, it is not surprising that a chemical structure isolated from a plant can actually have a microbial origin. Metagenomics provides a valuable tool to access the resources of bioactive compounds derived from unculturable microorganisms.

In this study, we have constructed a metagenomic library from endophytes and screened for antibacterial activity. The library was screened to select antimicrobial clones using *Staphylococcus aureus* as a target organism by the double-agar-layer method. One unique clone exhibiting antibacterial activity was selected from the metagenomic library. Secondary libraries were generated to obtain antibacterial subclones with reduced insert size for characterization of the gene responsible for the antibacterial activity.

The nucleotide sequence of the subclone was subjected to BLAST analyses against sequences present in the Genbank databases but no similarity to any known sequence was identified. The isolated gene encoded for a protein disclosed is in WO 2011/113999 and named as *Empetrum nigrum* metagenomic antibacterial protein 1 (En-MAP1, GenBank accession number KC466596). Analysis of the deduced amino acid sequence (SEQ D NO: 1) revealed that En-MAP1 encodes for a protein of 549 amino acids sharing the highest similarity of 32% to a hypothetical protein from *Pseudozyma hubeiensis* and no similarity to any protein of known function.

The isolated endophytic protein was expressed and isolated but no antimicrobial activity was observed. Antimicrobial activity of the in silico digested peptides was then predicted using algorithms described in the experimental part. The peptides were also tested for antimicrobial activity against *S. aureus*, *E. coli* and *Verticillium dahliae*. In preliminary tests some of the peptides predicted to have antimicrobial activity showed activity also in in vitro tests. Best candidates were selected for further studies.

Antimicrobial peptides interact with bacterial membranes to efficiently kill at optimum concentration. AMPs should also possess biocompatibility, salt tolerance and broad spectrum antimicrobial activity. By using rational design techniques, we were able to improve the peptide antimicrobial activity by incorporating or replacing various amino acids. We have designed and modified Met10 (Chain 100 defined by SEQ ID NO: 4), Met11 (Chain 200 defined by SEQ ID NO: 5), and Met12 (Chain 300 defined by SEQ ID NO: 6), peptides with tryptophan (W), arginine (R) and lysine (K) at various positions to improve antibacterial activity.

APD2 database was utilized to check the homology and identities of the peptides to known antimicrobials (Wang et al., 2009).

An embodiment of the invention is an antimicrobial peptide or a variant thereof comprising SEQ ID NO: 4 (Met 10, chain 100), SEQ ID NO: 5 (Met11, chain 200), SEQ ID NO: 6 (Met12, chain 300), or having at least 37% identity to SEQ ID NO: SEQ ID NO: 4, SEQ ID NO: 5 or SEQ ID NO: 6. It has surprisingly been found that relatively small fragments may have desired activity.

In one embodiment the peptide or a variant thereof comprises any of SEQ ID NO: 4, SEQ ID NO: 5 or SEQ ID NO: 6 or a peptide having at least 40%, preferably at least 50%, 60%, 70% identity to any of said sequences, more preferably at least 80% identity to any of said sequences and most preferably 90% or even 95% identity to said SEQ ID NO: 4, SEQ ID NO: 5 or SEQ ID NO: 6.

In this connection the term "identity" refers to the global identity between two amino acid sequences compared to each other from the first amino acid to the last corresponding amino acid. Thus a fragment can only be compared to respective amino acids (essentially equal number of amino acids) of the mature (poly) peptide.

In one embodiment of the invention the peptide comprising any of SEQ ID NO: 4, SEQ ID NO: 5 and SEQ ID NO: 6 is modified in order to increase antimicrobial activity.

According to one embodiment the peptide is modified with one or more of W, R, K, L, C, I, F and A-substitutions, more preferably with one or more of W, R and A-substitutions. These substitutions increase the interaction with microbial membranes and thereby improve antimicrobial activity.

In one embodiment the peptide defined by SEQ ID NO: 4 (chain 100) comprises one or more, preferably, five, six or even seven substitutions selected from the group consisting of V16K/L/W/R; Q15R/L/W/I/F/C; N14L/K/R/W; /W; A11W; M6W and I7W.

Preferably amino acid residues R8, L9 and H10 of SEQ ID NO: 4 are not modified.

According to one embodiment the peptide comprises one or more substitutions or deletions in SEQ ID NO: 4 (chain 100) selected from the group consisting of
a. D1-/R
b. C2-/K
c. W3-
d. S4-/R
e. A5-
f. M6W
g. I7W
h. A11W
i. Y13W/R
j. N14L/K
k. Q15R/L
l. V16K/W wherein "-" indicates deletion of the amino acid.

In one embodiment of the invention the peptide when compared to the original peptide defined by SEQ ID NO: 4 (chain 100), has 1 to 5, preferably 5 N-terminal amino acids been deleted. It has been found that the shorter peptides are able to maintain their antimicrobial activity. In addition shorter peptides result in lower cost of synthesis.

In a further embodiment the peptide variant of SEQ ID NO: 4 with N-terminal deletion further comprises one, two, three, four, five, six, seven or all amino acid modifications selected from the group consisting of V16K/W; Q15R/L; N14L/K; Y13R/W; A11W; I7W and M6W.

According to one embodiment the peptide defined by SEQ ID NO: 5 is modified with one or more of W, R, K, F, I and L-substitutions, more preferably with one or more of W, K and R-substitutions. These substitutions increase the interaction with microbial membranes and thereby improve antimicrobial activity.

In one embodiment the peptide defined by SEQ ID NO: 5 (chain 200) comprises one or more, preferably at least six, seven, eight, nine or even 10 substitutions selected from the group consisting of N1R/K/W, R2W, I3L, V4I/L, Q5W/K/R, Q6R/L/W, R7W, T8R/W/F, S9F/W/R/L and S10K/L.

Alternatively or in addition the peptide defined by SEQ ID NO: 5 can be modified by C-terminal addition of K (for example chain 207 defined by SEQ ID NO: 15)

In one embodiment amino acid residue R11 of peptide defined by SEQ ID NO: 5 is not modified.

According to one embodiment the peptide comprises one or more substitutions or deletions in SEQ ID NO: 5 (chain 200) selected from the group consisting of
a. N1K/R/W
b. R2W
c. I3L
d. V4I/L
e. Q5W/K/R
f. Q6R/L/W
g. R7W/R
h. T8R/W/F/K
i. S9F/W/R/L
j. S10K/L According to one embodiment the peptide defined by SEQ ID NO: 6 is modified with one or more of W, R, K, L, and I-substitutions, more preferably with one or more of W and R-substitutions. These substitutions increase the interaction with microbial membranes and thereby improve antimicrobial activity.

In one embodiment the peptide defined by SEQ ID NO: 6 (chain 300) comprises one or more, preferably four, five, six, seven, eight or even nine substitutions selected from the group consisting of Y1I/R/W/K, D2I/L/W/R, G4R/W, F5W/R, G6R/W/L, F8R, K9R, K10R and M11L/R/W/K.

Preferably amino acid residues K3 and L7 of the peptide defined by SEQ ID NO: 6 are not modified.

Alternatively or in addition the peptide defined by SEQ ID NO: 6 can be modified by addition of K between amino acid residues 9 and 10 (for example chain 313 defined by SEQ ID NO: 67).

According to one embodiment the peptide comprises one or more substitutions or deletions in SEQ ID NO: 6 (chain 300) selected from the group consisting of
a. Y1I/R/W/K
b. D2I/L/W/R
d. G4R/W
e. F5W/R
f. G6R/W/L
h. F8R
i. K9R
j. K10R
k. M11L/R/W/K.

In an embodiment the peptide or a variant thereof comprises a sequence selected from SEQ ID NO: 4 (chain 100) or one of SEQ ID NOs 7 to 31 (chains 101 to 125) or consists of it.

In an embodiment the peptide variant (peptide) comprises a sequence selected from SEQ ID NOs 7 to 15 (chains 101 to 109) or consists of it. In an embodiment the peptide variant comprises a sequence selected from SEQ ID NOs 10 to 15 (chains 104 to 109) or consists of it. In an embodiment the peptide variant comprises a sequence selected from SEQ ID NOs 10, 11 and 15 (chains 104, 105 and 109) or consists of it.

In an embodiment the peptide comprises SEQ ID NO: 4 (chain 100). In an embodiment the peptide consists of SEQ ID NO: 4 (chain 100).

In an embodiment the peptide or a variant thereof comprises a sequence selected from SEQ ID NO: 5 (chain 200) or one of SEQ ID NOs 32 to 54 (chains 201 to 223) or consists of it.

In an embodiment the peptide variant comprises a sequence selected from SEQ ID NOs 32 to 41 (chains 201 to 210) or consist of it. In an embodiment the peptide variant comprises a sequence selected from SEQ ID NOs 32, 34, 35 and 39 (chains 201, 203, 204 or 208) or consists of it.

In an embodiment the peptide comprises SEQ ID NO: 5 (chain 200). In an embodiment the peptide consists of SEQ ID NO: 5 (chain 200).

In an embodiment the peptide or a variant thereof comprises a sequence selected from SEQ ID NO: 6 (chain 300) or one of SEQ ID NOs 55 to 79 (chains 301 to 325) or consists of it.

In an embodiment the peptide variant comprises a sequence selected from SEQ ID NOs 55 to 67 (chains 301 to 313) or consists of it. In an embodiment the peptide variant comprises a sequence selected from SEQ ID NOs 55, 58, 59 and 61 to 65 (chains 301, 304, 305 or 307 to 311) or consists of it.

In an embodiment the peptide variant comprises a sequence selected from SEQ ID NOs 61 and 62 (chains 307 and 308) or consists of it.

In an embodiment the peptide comprises SEQ ID NO: 6 (chain 300). In an embodiment the peptide consists of SEQ ID NO: 6 (chain 300).

It is evident that peptides and their variants have different antimicrobial activities against different microbes. In this study antimicrobial activity was tested against both bacteria and fungi.

Antibacterial activity of selected peptides (peptide variants) was tested against *Escherichia coli* (ATCC 25922), *Klebsiella pneumoniae* (ATCC 10031), *Pseudomonas aeruginosa* (ATCC 27853) and *Staphylococcus aureus* (ATCC 25923). Radial diffusion assay and minimum inhibitory concentration was used to determine the antibacterial activity, where radial diffusion assay was used to asses the antifungal activity of the peptide variants.

Antifungal activity was tested against *Aspergillus flavus* (DSM 1959) and *Penicillium chrysogenum* (DSM 1075).

In an embodiment the peptide or a fragment thereof is chemically synthesized (synthetic peptide). In another embodiment the peptide has been recombinantly produced. In one embodiment the peptide or peptides are isolated from the growth medium of recombinant peptide production or synthesis medium.

In one embodiment, the antimicrobial peptide is attached to a surface of a medical device, food package, carrier substance or e.g. biosensor, optionally using a linker peptide. Alternatively or in addition, in another embodiment the peptide is attached to detectable agents such as for example fluorescent agent or an enzyme substrate for example when using the antimicrobial peptide in biosensors. In one embodiment, said peptides are immobilized on silicon, polyethene, and other materials in order to be used as medicine or coating agents.

In hemolysis assays, the ability of peptides at 128 μg/ml concentration to lyse human erythrocytes to release hemoglobin was measured. The peptides described here preferably have low hemolytic activity (0.2 to 3.8% hemolysis) in mammal body. The hemolytic concentration tested (128 μg/ml) is more than 50 fold of minimal inhibitory concentration (MIC) of chains 105, 201 and 308 and hemolysis is negligible at 0.2-0.5% respectively. These peptides are useful as antimicrobial drugs as they show little or no side effects at concentrations needed to kill bacteria.

In one embodiment the peptide or a variant thereof exhibits an activity against microorganisms, in particular against gram positive and gram negative bacteria, in particular against the families Staphylococcaceae and Enterobacteriaceae. In one embodiment the peptide exhibits an activity against yeast and/or fungi.

In one embodiment the peptide or a variant thereof exhibits an activity against bacteria. In one embodiment the peptide or a variant thereof exhibits an activity against fungi. In one embodiment the peptide or a variant thereof exhibits an activity against bacteria and fungi. Activity against bacteria and/or fungi can be for example suppression of multiplication or growth of said microbes or killing them.

In one embodiment the peptide or a variant thereof exhibits an activity against gram positive bacteria, in particular microorganisms of the family Staphylococcaceae, in particular against microorganisms of the species *S. aureus*.

Peptides comprising essentially any of SEQ ID NOs: 10 to 15 (Chains 104 to 109), SEQ ID NOs: 32, 34 to 36, 39 to 41 (Chains 201, 203 to 205, 208 to 210) and SEQ ID NOs: 55 to 65 and 67 (Chains 301 to 311 and 313) are particularly active against Staphylococcaceae, particularly *S. aureus*. *S. aureus* has developed resistance to most of the commercially available antibiotics. Antimicrobial peptides as we describe here, are a promising class of new antibiotics, as they do not induce resistance in microorganisms.

In one embodiment the peptide exhibits an activity against gram negative bacteria, in particular against *E. coli*. Peptides comprising essentially any of SEQ ID NOs: 10 to 15 (Chains 104 to 109), SEQ ID NOs: 32, 34 to 36, 39 to 41 (Chains 201, 203 to 206, 208 to 210) and SEQ ID NOs: 55 to 65 and 67 (Chains 301 to 311 and 313) are particularly active against *E. coli*.

In one embodiment the peptide exhibits an activity against *Klebsiella*, particularly *Klebsiella pneumoniae*. Peptides comprising essentially any of SEQ ID NOs: 10 to 15 (Chains 104 to 109), SEQ ID NOs: 32, 34, 35, 39 to 41 (Chains 201, 203, 204, 208 to 210) and SEQ ID NOs: 55, 58, 59, 61 to 65, and 67 (Chains 301, 304, 305, 307 to 311 to 311 and 313) are particularly active against *Klebsiella*.

In one embodiment the peptide exhibits an activity against *Pseudomonas*, particularly *Pseudomonas aeruginosa*. Peptides comprising essentially any of SEQ ID NOs: 10 to 12 and 15 (Chains 104 to 106, 109), SEQ ID NOs: 32, 34, 35 and 39 (Chains 201, 203, 204, 208) and SEQ ID NOs: 55 to 65 and 67 (Chains 301 to 311 and 313), are particularly active against *Pseudomonas*.

In one embodiment the peptide exhibits an activity against Aspergilli, particularly *A. flavus*. Peptides comprising essentially any of SEQ ID NO: 10, 11 or 15, SEQ ID NO: 32 or 35 (Chains 104, 105 or 109), SEQ ID NOs: 32 or 35 (chains 201 or 204); SEQ ID NOs: 60, 61, 62 and 64 (chains 306, 307, 308 and 310) are particularly active against Aspergilli.

In one embodiment the peptide exhibits an activity against *Penicillium*, particularly *P. chrysogenum*. Peptides comprising essentially any of SEQ ID NO: 10, 11 or 15, SEQ ID NO: 32 or 35 (Chains 104, 105 or 109), SEQ ID NOs: 32 or 35 (chains 201 or 204); SEQ ID NOs: 60, 61, 62 and 64 (chains 306, 307, 308 and 310) are particularly active against *Penicillium*.

In one embodiment the peptide exhibits an activity against clinical strains of *E. coli, K. pneumoniae, E. cloacae, P. aeruginosa, Serratia marcescens, Proteus mirabilis, S. pneumoniae, Acinetobacter baumannii, A. johnsonii, S. aureus, Candida albicans, C. glabrata, C. parapsilosis* and *C. quillermondiae*. Peptides comprising essentially any of SEQ ID NO: 10, 11 or 15, SEQ ID NO: 32 or 35 (Chains 104, 105 or 109), SEQ ID NOs: 32 or 35 (chains 201 or 204); SEQ ID NOs: 58, 60, 61, 62, 63, 64 and 65 (chains 304, 306, 307, 308, 309, 310 and 311).

Chain 104, chain 105, chain 109, chain 201, chain 204, chain 307, chain 308 and chain 310 are demonstrably broad-spectrum antimicrobial peptides, active against gram positive and negative bacteria in a range of 0.5 to 32 μg/ml and has little side effects to humans as tested by hemolysis assay.

The present invention relates also to an antimicrobial composition comprising an antimicrobial peptide or peptides here described. In an embodiment such composition further comprises a pharmaceutically acceptable carrier and optionally other conventional ingredients.

Peptide having SEQ ID NO: 4 (chain 100), SEQ ID NO: 5 (chain 200), SEQ ID NO: 6 (chain 300) or a variant thereof having at least 37%, preferably at least 40%, 50%, 60%, 70%, more preferably at least 80% and most preferably at least 90% identity to said sequence or any peptide according to the present disclosure for use in therapy, particularly for use as an antimicrobial agent.

The antimicrobial activity can be against bacteria or fungi or bacteria and fungi. The bacteria can be gram positive or gram negative bacteria. In particularly the peptide has activity against microorganisms of the genera Staphylococcus or E. coli or both Staphylococcus and E. coli. Various antimicrobial activities and hemolytic properties of the peptides have been discussed above.

One further embodiment of the invention is a use of the peptide according to the present disclosure as a medicament, feed additive, preservative or surfactant.

In one embodiment a peptide having any of SEQ ID NO: 4, 5 or 6 or a variant thereof having at least 37%, preferably at least 40%, 50%, 60%, 70%, more preferably at least 80% and most preferably at least 90% identity to said sequence or any peptide according to the present disclosure is used as a medicament, especially as a medicament against contaminating microbes including S. aureus discussed above.

The present invention relates also to a use of the peptide(s) and their variants described here as a medicament, feed additive, preservative or surfactant is claimed. The toxins produced by various microorganisms contaminate human foods and animal feeds and these peptides used as preservatives may reduce the growth of the contaminants. The activities and other properties of the peptides have been discussed above in connection of other embodiments.

Peptides chain 104, chain 105, chain 109, chain 201, chain 204, chain 307, chain 308 and chain 310 are demonstrably broad-spectrum antimicrobial peptides, active against gram positive and negative bacteria in a range of 0.5 to 32 µg/ml and has little side effects to humans as tested by hemolysis assay. These peptides has a potential for treatment against gram negative infections caused by *Escherichia coli* (ATCC 25922), *Klebsiella pneumoniae* (ATCC 10031), *Pseudomonas aeruginosa* (ATCC 27853) and gram positive *Staphylococcus aureus* (ATCC 25923).

The present invention relates also to a method of killing or inhibiting growth of microbes, comprising the step of treating said microbes with a peptide(s) or their variants described here. In one embodiment the peptide or a variant there of exhibits an activity against microorganisms, in particular against gram positive and/or gram negative bacteria, in particular against the families Staphylococcaceae and Enterobacteriaceae, in particular against microorganisms of the species S. aureus and/or E. coli. In one embodiment the peptide or a variant thereof exhibits an activity against fungi. In still further embodiment the peptide or a variant thereof exhibits activity against both fungi and bacteria. The activities and other properties of the peptides have been discussed above in connection of other embodiments.

Catheter acts as a carrier of bacteria through attachment to the surface and then to the lumen of urethra. Most of the catheters are made of silicone rubber where microbes adhere easily to form biofilms and cause infections. Several strategies have been developed to overcome these problems by using antibiotic compounds such as rifampin and minocycline, or silver coating on catheter surfaces. However, the use of antibiotics risk development of bacterial resistance and antibiotic efficacy in the clinical applications is not well known. Silver-coated catheters were found ineffective in in-vitro studies.

Catheter-associated urinary tract infections (CAUTI) can be prevented by using antimicrobial peptide (AMP)-coated urinary catheters, which also prevent the spread of antibiotic resistance.

It should also be understood that the peptide(s) or their variants of the present invention can be used with various uses requiring antimicrobial activity.

It is to be understood that the terminology employed herein is for the purpose of description and should not be regarded as limiting.

The features of the invention described here as separate embodiments may also be provided in combination in a single embodiment. Also various features of the invention described here in the context of a single embodiment, may also be provided separately or in any suitable sub-combination. It should be understood, that the embodiments given in the description above are for illustrative purposes only, and that various changes and modifications are possible within the scope of the disclosure.

A listing of the cited references will be given below. The contents of all citations are herewith incorporated by reference.

The following non-limiting examples illustrate the invention.

EXAMPLES

Example 1: Total Plant DNA Isolation

Fresh and young leaves of *Empetrum nigrum* L. were surface sterilized with 70% ethanol (v/v) for 1 min and in sodium hypochlorite (3.5% v/v) for 5 min and used for the isolation of genomic DNA (Pirttilä et al. 2001).

Example 2: Metagenomic Library Construction and Screening for Antibacterial Activity Plant DNA isolated from *E. nigrum* was dissolved in sterile water to a concentration of 0.1 µg µl$^{-1}$. The DNA was then subjected to preparative pulsed-field gel electrophoresis in a CHEF-DRII (Bio-Rad) system. The electrophoresis conditions (pulse intervals and durations) were: N/S—60 s and E/W—60 s for 6 h; N/S—90 s and E/W—90 s for 6 h; N/S—99 s and E/W—99 s for 6 h, respectively, with a voltage of 6 V/cm, a 120° fixed angle and using a 0.15× Tris-borate-EDTA (TBE) buffer. During the electrophoresis, the temperature was maintained at 10° C. After electrophoresis, a strip from each side of the gel was cut off and stained with ethidium bromide to visualize the DNA. The high-molecular-weight DNA was then excised from the remaining unstained part of the gel and electro-eluted for 1 h at 100 V in a dialysis bag containing 0.5×TBE. Amplification by primers specific for fungi and bacteria was done as previously (Koskimäki et al. 2010, Tejesvi et al. 2010) to confirm the separation of microbial DNA. For cloning, the DNA of about 25-30 kb was end repaired to produce 5'-phosphorylated DNA and ligated to blunt-ended dephosphorylated pCC1FOS™ vector. The ligation mixture was packaged into lambda phages using MaxPlax Lambda Packaging Extracts (Epicentre). The packaged library was then transduced into *E. coli* EPI-300, and the transformants were selected on LB agar plates supplemented with chloramphenicol. The packaged fosmid library was stored in cryotubes as clone pools containing approximately $10^3$ clones per pool until screening.

The fosmid library screening was performed as follows: clone pools were thawed and spread onto 150-mm LB agar plates supplemented with chloramphenicol to obtain ~1000 colonies per plate. The library plates were incubated overnight at 30° C. followed by incubation at room temperature (RT) for additional 3-5 days. The plates were overlaid with top agar containing exponentially growing *Staphylococcus aureus* and incubated overnight at 37° C., followed by further incubation at RT for 3-5 days. Colonies with antibacterial activity were identified by a zone of inhibition of *S. aureus* growth. Such colonies were picked through the top agar and separated from the chloramphenicol-sensitive assay strain (*S. aureus*) by streaking onto LB plates containing ampicillin and chloramphenicol. Restriction analysis of the selected antibacterial fosmid clone was carried out by digestion with BamHI and electrophoresis.

Example 3: Strains, Plasmids and Growth Conditions

EPI-300™-T1® Phage T1-resistant *E. coli* cultures were grown at 37° C. on Luria-Bertani (LB) agar or in LB broth+10 mM $MgSO_4$ supplemented with the appropriate antibiotics. The following antibiotic concentrations were used for the *E. coli* strain: chloramphenicol 12.5 µg $ml^{-1}$ and ampicillin 100 µg $ml^{-1}$. Plasmid pCC1FOS™ (Epicentre, Madison, USA) that carries two origins of replication, a single copy origin (ori2) and an inducible high copy origin (oriV) was used to construct the metagenomic library from endophytes of *Empetrum nigrum* and for subcloning the genes conferring such antibacterial activity. The pET11-c vector was used to express the genes responsible for the antibacterial activity in the host strain *E. coli* BL21 (DE3) gold.

Example 4: Subcloning and Sequencing of Clone pFosS1A

The antibacterial fosmid clone selected from the agar overlay assay was named pFosS1. The metagenomic fosmid was isolated using the Plasmid Midiprep Kit (Qiagen) and subjected to partial digestion with Sau3AI (0.1 U $\mu l^{-1}$ of DNA, 37° C. for 15 min) and electrophoresis for size selection of the DNA and subcloning. Fragments greater than 1.5 kb were extracted from the gel, end-repaired and ligated into blunt-ended dephosphorylated pCC1FOS™. The ligation mixture was transformed into *E. coli* and the recombinant clones were screened by the agar overlay assay and spread onto LB plates supplemented with chloramphenicol. The subclones showing clear zones of inhibition of *S. aureus* were analysed by gel electrophoresis after digestion with BamHI to select the subclone harboring the smallest insert of ~1.8 kb. This subclone was named pFosS1A and sequenced with the primers pCC1 forward and pCC1 reverse according to the manufacturer's instructions (Abi 3730 DNA Analyser, Abi Prism BigDye Terminator Cycle Sequencing Kit, Applied Biosystems, Warrington, UK). The open reading frame contained within the subclone pFosS1A was named En-MAP1 and analyzed by the BLAST program of Genbank as well as SignalP and pfam.

Example 5. Construction and Screening of the Metagenomic Library

The band corresponding to endophytic DNA was separated from the *Empetrum nigrum* genomic DNA, which remained in the wells of the agarose gel after PFGE electrophoresis. Presence of endophytic DNA in the band was confirmed by amplification of PCR products with primers specific for fungi and bacteria. Approximately 8,000 metagenomic clones were obtained from 20 µg DNA. Screening of the metagenomic library by the agar overlay method resulted in the identification of one antibacterial clone exhibiting an inhibition zone for *S. aureus*. However, growth inhibition of the host *E. coli* was not observed. Restriction fragment analysis revealed that the clone carried an insert DNA of over 30 kb in size. A secondary library was generated from the antibacterial clone to select antibacterial subclones and to characterize the individual gene(s) responsible for the antibacterial activity. Restriction fragment analysis of antibacterial subclones identified the smallest insert of 1.8 kb in subclone pFosS1A, which still exhibited growth inhibition of *S. aureus* in the agar overlay assay (FIG. 1).

Example 6: Fractionation and Analysis of Clone Supernatant

*E. coli* cells carrying the subclone pFosS1A and control (empty vector) were grown overnight at 37° C. in LB-broth containing chloramphenicol. These cultures were used as inocula for the copy number amplification procedure. One volume of these cultures was added to 10 volumes of fresh LB+chloramphenicol and 1/100 of CopyControl Induction Solution (Epicentre) was added to the media to induce clones to high copy number. After vigorous shaking of cultures at 37° C. for 20 h, the supernatant was separated from bacterial cells by centrifugation for 20 min at 3040×g at 4° C. The supernatant was freeze-dried by Heto PowerDry LL1500 freeze dryer (ThermoElectron, Mukarov, Czech Republic). The freeze-dried broth was weighed and 50 mg was dissolved to 2 ml of distilled water. The material was kept in ultrasonicator for 20 minutes, centrifuged for 10 minutes, filtered (GHP Bulk Acrodisc 13, Pall Life Sciences) and fractionated by semi preparative High Pressure Liquid Chromatography (HPLC). The fractions were then tested for antibacterial activity by the 96-well plate standard method using *S. aureus* as the test strain. Supernatants of subclone pFosS1A and control were analyzed for small molecules by Alliance 2690 HPLC (Waters, Milford, Mass., USA) combined with Micromass LCT Time-of-flight mass spectrometry (TOFMS) (Micromass, Altrincham, UK).

Example 7. Sequence Analysis of the Antibacterial Subclone

The insert of subclone pFosS1A was completely sequenced in both directions and it contained a unique open reading frame of ~1650 bp. The putative ribosome-binding site and promoter sequence are present at ~35/−10 upstream region from the initiation codon. The nucleotide sequence was subjected to BLAST analyses against sequences present in the Genbank databases but no similarity to any known sequence was identified. This suggested that the isolated gene encoded for a protein of novel structure and therefore the protein was named *Empetrum nigrum* metagenomic antibacterial protein 1 (En-MAP1). Analysis of the deduced amino acid sequence revealed that En-MAP1 encodes for a protein of 549 amino acids (FIG. 2), sharing the highest similarity of 32% to a hypothetical protein from *Pseudozyma hubeiensis* and no similarity to any protein of known function. SignalP analysis indicated that the amino acid sequence of En-MAP1 had no putative amino-terminal signal sequences for secretion or translocation. When the deduced amino acid sequence was analyzed for conserved motifs using the pfam protein family database, three pentatricopeptide repeat-motifs were identified at positions 77 to 107, 126 to 153 and 392 to 420 aa (FIG. 2). En-MAP1 was predicted to be a soluble protein having no transmembrane region analyzed by TMpred and PSORT. The residues 147-176 also consisted a predicted coil-coil region, which is typical for proteins involved in protein-protein interactions, and a possible leucine zipper starting at residue 490, analyzed by PSORT.

Example 8: Protein Expression in pET23(b)

The gene En-MAP1 was amplified using primers with Nde1 and Sal1 restriction sites pFosS1F (CATATGAGACTAGTAGCTCATCCTGTTCCTGATGC; SEQ ID NO: 2) and pFosS1R (GTCGACTTATTAACGAGATGACGTCCTCTGCTGTACG; SEQ ID NO: 3). The amplification products were cloned into pET23(b) vectors, transformed into XL1 competent cells, and the gene identity was confirmed by sequencing. The expression studies were done using *E. coli* strains BL21 pLysS and BL21 pRARE as the hosts. The protein was expressed in both strains as inclusion bodies, which were isolated (van Lith et al. 2007). The inclusion bodies were suspended in 5M guanidine hydrochloride/0.2 M sodium phosphate buffer (pH 7.0) and the protein was refolded on HisTrap Column (GE Healthcare Life Sciences) using a linear buffer exchange from 3 M guanidine/0.2 M sodium phosphate (pH 7.0) to 0.2 M sodium phosphate (pH 7.0) over 4 h in AKTA FPLC, and finally eluted with 50 mM EDTA/20 mM sodium phosphate buffer (pH 7.0). The nucleotide sequence of En-MAP1 has been deposited to the GenBank under accession number KC466596.

Example 9: Antibacterial Activity Analysis of Protein

Both folded and unfolded proteins were tested for antibacterial activity against *S. aureus* by pipetting 10 µg of protein on the *S. aureus* culture on an LB plate. The activity was also tested in folded and unfolded protein digested with trypsin in 0.01% acetic acid at concentrations of 30 and 60 µg/ml.

Example 10: Prediction of Antimicrobial Peptides and Peptide Synthesis

The protein En-MAP1 was in silico-trypsin digested <(http://au.expasy.org)> and 12 peptides (Met1-Met12) were predicted <(http://www.bicnirrh.res.in/antimicrobial)> to be antimicrobial by three different algorithms (Support Vector Machine (SVM) classifier, Random Forest Classifier and Discriminant Analysis Classifier) and by APD2 <(http://aps.unmc.edu/AP/prediction/prediction_main.php)>. Synthesized peptides were purchased from GenScript, USA.

Example 11: Antimicrobial Activity of Synthesized Peptides

The radial diffusion assay (RDA) was carried out as described by Andersen et al. (2010). Briefly, 30 ml of 1/10 Muller-Hinton broth (MHB) supplemented with 1% agarose and $5.0 \times 10^5$ CFU/ml *S. aureus* or *E. coli* or *K. pneumoniae*, *P. aeruginosa* cells was poured into a single-well omnitray (Nunc) and overlaid with a TSP 96-well plate. One hundred µg of each synthesized peptide was tested. The peptides were also tested against *Fusarium oxysporum* and *Verticillium dahliae*, for which 1/3 potato dextrose agarose was used. To test the synergistic effect of peptides, each peptide was mixed in equimolar concentrations. Mix1 (met1-12), Mix2 (met3, 4 and 5), Mix3 (met 8, 9 and 10), Mix 4 (met11, 12) and Mix5 (8, 9, 10, 11, 12) were prepared and tested against *E. coli* and *S. aureus*. Gentamicin and vancomycin were included as positive controls for bacteria and amphotericin B was used as the control for fungi.

Minimum inhibition concentrations (MICs) were determined against *Escherichia coli* (ATCC 25922), *Staphylococcus aureus* (ATCC 25923), *Klebsiella pneumoniae* (ATCC 10031) and *Pseudomonas aeruginosa* (ATCC 27853). Also clinical strains of *E. coli*, *K. pneumoniae*, *E. cloacae*, *P. aeruginosa*, *Serratia marcescens*, *Proteus mirabilis*, *S. pneumoniae*, *Acinetobacter baumannii*, *A. johnsonii* and *S. aureus* were used for MICs assays. Additionally, clinical strains of yeast including *Candida albicans, C. glabrata, C. parapsilosis* and *C. quillermondiae* were used. The susceptibility of these microorganisms to Chain peptides were determined using micro broth dilution assay. Colonies of the respective microorganism from Muller Hinton (MH) agar plates incubated overnight were suspended in MH broth media and final concentration of microorganism was adjusted to $5.0 \times 10^5$ cfu/ml. An aliquot of 10 µl of each Chain peptide, or gentamicin, tetracycline as reference antibiotics were added in differing concentrations along with 90 µl of bacterial suspension to 96 well polypropylene plates and incubated at 37° C. for 20 to 24 hours. Concentrations of Chain peptides and reference antibiotics ranged from 0.125 to 128 µg/ml and the MICs were recorded as the lowest concentration with no visual growth of bacteria. Similarly, antifungal MICs were tested in Potato dextrose broth.

Example 12: Expression Analysis of the Antibacterial Clone

The subclone expressing pFosS1A was analyzed by HPLC-MS for possible production of small antimicrobial molecules in the liquid medium and compared with the control (empty vector). The chromatograms and spectra of the peaks for the antibacterial clone and the control were identical. The medium was fractioned and tested for antibacterial activity against *S. aureus*, but no activity was detected. This suggested that the antibacterial activity against *S. aureus* was not from a metabolite generated by En-MAP1 activity.

The gene En-MAP1 was then cloned into the expression plasmid pET23(b) to analyze whether the antibacterial activity was due to the protein itself. The resulting construct pET23(b)-FosS1A contained the En-MAP1 gene in-frame. When transformed into *E. coli* expression strain BL21 (DE3) pLyseS and BL21 (DE3) pRARE, a protein of approximately 63 kDa (predicted mass 63.3 kDa) was produced in the cell extracts of induced, but not in the uninduced cultures. The resulting protein includes the amino acid sequence MHHHHHHM- (SEQ ID NO: 80) prior to the first amino acid of the protein sequence. The protein was expressed in both strains as inclusion bodies and they were purified and folded in a His-Trap column, resulting in about ~1 mg of pure folded protein. The folded protein was tested for antibacterial activity against *S. aureus* and no activity was observed. To test whether a shorter fragment was responsible for the antibacterial activity due to alternative translation starting sites, three constructs encoding shorter fragments of En-MAP1 were designed and expressed, but no activity was observed. However, when the folded full En-MAP1 protein (SEQ ID NO: 1) was digested with trypsin, antibacterial activity was observed for up to two hours after digestion (data not shown). No activity was detected in the trypsin digest of the unfolded protein. This suggested that the antimicrobial activity resulted from fragmentation of the protein, producing a peptide, which contained an internal trypsin cleavage site that was protected by the folded structure.

To further identify the peptide responsible for antimicrobial activity, the En-MAP1 protein was digested in silico and the peptides, which were predicted to be antimicrobial, were synthesized. Cleavage sites for several restriction enzymes, proteases and chemical compounds, such as ArgC proteinase, Asp-N endopeptidase (EC 3.4.24.33), chymotrypsin-HS30 (EC 3.4.21.1), clostripain, CNBr (EC 208-051-2), formic acid, Lys-C, iodosobenzoic acid, proline endopeptidase, and trypsin were included in the in-silico analysis. Antimicrobial activities of the peptide fragments were predicted using four different algorithms (Support Vector Machine (SVM) classifier, Random Forest Classifier, Discriminant Analysis Classifier and APD2).

Figure 3:
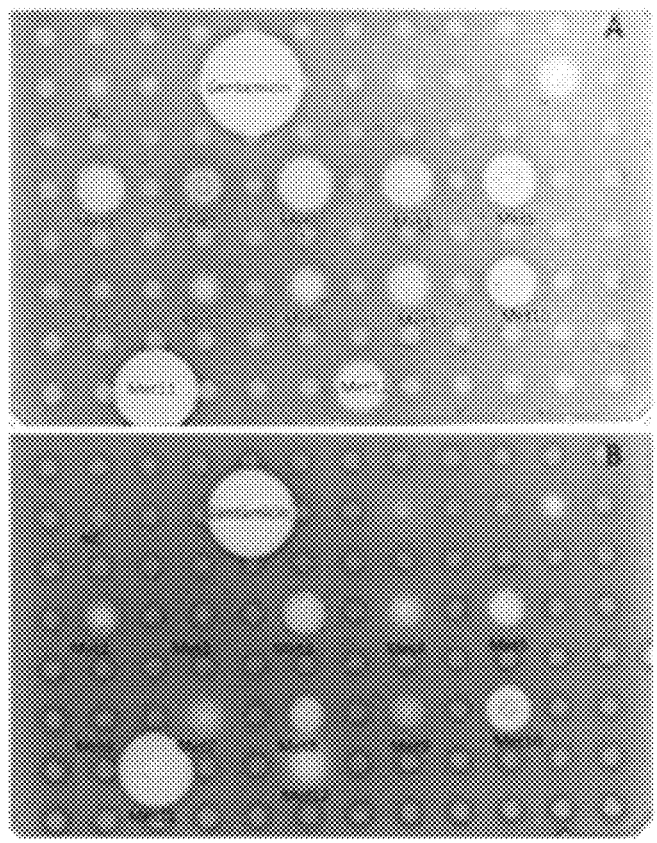
FIG. 3. The representative Radial Diffusion assay (RDA) of synthesized peptides Met1-Met12, 100 µg each, tested against *E. coli* (A) and *S. aureus* (B) NC=negative control, Gentamicin 10 µg.

The majority of these peptides were from tryptic digest predictions, while three peptides (shown as Met10, Met11 and Met12 in FIG. 3 and Chain 100 defined by SEQ ID NO: 4, Chain 200 defined by SEQ ID NO: 5 and Chain 300 defined by SEQ ID NO: 6, respectively in tables (1, 2a, 2b, 2c, 3a, 3b and 3c) and sequence listing) resulted from Asp-N-endopeptidase16, chymotrypsin-HS30 and CnBr digestions, respectively. Eight of these peptides contained an internal trypsin cleavage site.

Example 13: Salt, pH and Thermal Stability

Thermal stability was evaluated by diluting peptides to the concentration of 2 mg/ml in PBS buffer (pH 7.4) and incubating at different temperatures, such as +4° C., 25° C. (RT), 37° C. and 45° C., peptides stored at −20° C. were used as control. After each time interval, 100 µl (2 mg/ml) of peptides were taken and stored at −20° C. for radial diffusion assay to determine the antibacterial activity (FIG. 8). Peptides were also tested by diluting them at different pH values starting from pH 4 to 9. The effect of NaCl on the antimicrobial activity was tested by adding different concentrations (50, 100 and 200 mM) of NaCl to MH medium and the minimum inhibitory concentrations were tested against 4 ATCC bacterial strains.

Example 15: Bacterial Adherence on Coated and Uncoated Silicon Catheters

The coated (Chain 105 or Chain 201) and uncoated silicon catheters were cut into 0.5 cm pieces and placed in 24 well plates suspended with 1 ml of $5 \times 10^5$ CFU/mL bacterial (*E. coli* and *S. aureus*) culture in phosphate buffer saline (PBS). Samples were incubated at 37° C. for 6 h at 150 RPM. After incubation, each catheter piece was rinsed with 1 ml of PBS for 2 times using fresh PBS. The catheter pieces were transferred to Eppendorf tubes and 500 µl of PBS was added, sonicated in water bath for 2 minutes, vortexed for 5 sec, serially diluted, and CFUs were determined.

Example 14: Preparation of Cells for Transmission Electron Microscopy (TEM)

*E. coli* and *S. aureus* were grown to mid-exponential phase and diluted in Muller Hinton broth (MHB) medium to a cell density of 0.1 by taking absorbance at 600 nm and incubated at 37° C. for 1 h with 10 µg/ml Chain peptides. After incubation, an equal volume of 2% glutaraldehyde in 0.1 M phosphate buffer was added and the cells were pelleted by centrifugation at 5000 rpm for 2 minutes, and the cell pellet was fixed with 1% glutaraldehyde in 0.1 M phosphate. Cells were post-fixed with osmium tetroxide, dehydrated using increasing concentrations of acetone or alcohol, and embedded in plastic resin (Epon). Ultrathin sections (70-80 nm) were post-stained with uranyl acetate and lead citrate before observation with TEM. Microscopy was performed with a Tecnai G2 Spirit 120 kV TEM with Veleta and Quemesa CCD cameras.

TABLE 1

The peptide variants generated using tryptophan, lysine and arginine residues at various places and predicted by statistical models using CAMP database (SVM, RF, ANN and DA).

| Sl. No | Name | Sequence | SVM values[a] | RF values[b] | ANN[c] | DA values[d] | Aliphatic Index[e] | Instability Index[f] | Net charge | Identities | CAMP database[g] |
|---|---|---|---|---|---|---|---|---|---|---|---|
| 4 | Chain100 | DCWSAMIRLHAKYNQV | 0.156 | 0.4615 | AMP | 0.012 | 79 | 14.7 | 1 | 6/11 (54%) | CAMPSQ4068 |
| 7 | Chain101 | KIRLHRKRLRK | 0.976 | 0.725 | AMP | 0.995 | 106 | 48 | 7 | 6/11 (54%) | CAMPSQ73 |
| 8 | Chain102 | KKRLHRKRLRK | 0.997 | 0.6695 | AMP | 0.995 | 70 | 85 | 8 | 8/11 (72%) | gi_33736048 |
| 9 | Chain103 | KLRLHAKRLRK | 0.893 | 0.696 | AMP | 0.922 | 115 | 66 | 6 | No hits | nil |
| 10 | Chain104 | RKWRAMIRLHAKRLRK | 0.989 | 0.7955 | AMP | 0.871 | 85 | 41 | 8 | 6/11 (54%) | gi_74472293 |
| 11 | Chain105 | RKWRAMIRLHAKWLRK | 0.997 | 0.8375 | AMP | 0.852 | 85 | 29 | 7 | 6/11 (54%) | gi_67584689 |
| 12 | Chain106 | WIRLHWKRLRK | 1 | 0.927 | AMP | 0.995 | 106 | 53 | 5 | 5/11 (45%) | gi_59754113 |
| 13 | Chain107 | WWRLHAKKKLW | 1 | 0.97 | AMP | 0.993 | 80 | 22.9 | 4 | 4/11 (36%) | CAMPSQ4044 |
| 14 | Chain108 | WWRLHAKRKLW | 1 | 0.936 | AMP | 0.994 | 80 | 52 | 4 | 6/11 (54%) | CAMPSQ4044 |
| 15 | Chain109 | WWRLHAKWKLW | 1 | 0.9765 | AMP | 0.996 | 80 | 22 | 3 | 4/11 (36%) | gi_59754171 |
| 16 | Chain110 | KLKRAMIRLHAKKRLK | 0.916 | 0.8285 | AMP | 0.926 | 110 | 34 | 8 | 7/16 (44%) | gi_75999248 |
| 17 | Chain111 | KLKRAMIRLHAKKWRW | 0.996 | 0.869 | AMP | 0.816 | 85 | 54 | 7 | No hits | nil |
| 18 | Chain112 | RLKRAMIRLHAKKWRW | 0.995 | 0.861 | AMP | 0.826 | 85 | 60 | 7 | No hits | nil |
| 19 | Chain113 | RWWRAMIRLHAKKWRW | 1 | 0.8495 | AMP | 0.97 | 61 | 80 | 6 | 7/16 (44%) | gi_59754035 |
| 20 | Chain114 | WWRLHAAKKIL | 1 | 0.9625 | AMP | 0.991 | 124 | 19 | 3 | 5/11 (45%) | CAMPSQ4137 |
| 21 | Chain115 | WWRLHAKKKCW | 0.998 | 0.9205 | AMP | 0.97 | 45 | 30 | 4 | 4/11 (36%) | CAMPSQ4044 |
| 22 | Chain116 | WWRLHAKKKFW | 1 | 0.954 | AMP | 0.995 | 45 | 9.09 | 4 | 4/11 (36%) | CAMPSQ4044 |
| 23 | Chain117 | WWRLHAKKKIW | 1 | 0.969 | AMP | 0.993 | 80 | 1.37 | 4 | 3/11 (27%) | CAMPSQ4009 |
| 24 | Chain118 | WWRLHAKKKRW | 1 | 0.9075 | AMP | 0.996 | 45 | 90 | 5 | 5/11 (45%) | gi_3407608 |
| 25 | Chain119 | WWRLHAKKKWR | 1 | 0.907 | AMP | 0.993 | 45 | 9 | 5 | 4/11 (35%) | gi_59754211 |

TABLE 1-continued

The peptide variants generated using tryptophan, lysine and arginine residues at various places and predicted by statistical models using CAMP database (SVM, RF, ANN and DA).

| Sl. No | Name | Sequence | SVM values[a] | RF values[b] | ANN[c] | DA values[d] | Aliphatic Index[e] | Instability Index[f] | Net charge | Identities | CAMP database[g] |
|---|---|---|---|---|---|---|---|---|---|---|---|
| 26 | Chain120 | WWRLHAKKKWW | 1 | 0.968 | AMP | 0.998 | 45 | 9.09 | 4 | 5/11 (45%) | CAMPSQ4044 |
| 27 | Chain121 | WWRLHAKLKLW | 1 | 0.9585 | AMP | 0.995 | 115 | 7.4 | 3 | 4/11 (36%) | CAMPSQ4044 |
| 28 | Chain122 | WWRLHAKRKRW | 1 | 0.8155 | AMP | 0.997 | 44 | 120 | 5 | 5/11 (45%) | gi_3407608 |
| 29 | Chain123 | WWRLHAKWRWR | 1 | 0.928 | AMP | 0.998 | 44 | 61 | 4 | 6/11 (54%) | gi_59754169 |
| 30 | Chain124 | WWRLHARKRWW | 1 | 0.933 | AMP | 0.999 | 44 | 90 | 4 | 5/11 (45%) | gi_3407608 |
| 31 | Chain125 | WWRLHAWKWRR | 1 | 0.936 | AMP | 0.998 | 44 | 61 | 4 | 7/11 (63%) | gi_59754006 |
| 5 | Chain200 | NRIVQQRTSSR | 0.028 | 0.3175 | NAMP | 0.006 | 61 | 53 | 3 | No hits found | nil |
| 32 | Chain201 | KWIVWRWRFKR | 1 | 0.977 | AMP | 0.96 | 61 | 69 | 5 | 6/11 (54%) | gi_59754085 |
| 33 | Chain202 | RKIVKKRTFKR | 0.988 | 0.6975 | AMP | 0.997 | 61 | 47 | 7 | 6/11 (54%) | gi_33735965 |
| 34 | Chain203 | RRIVKLRWFKR | 1 | 0.8035 | AMP | 0.944 | 97 | 128 | 6 | No hits | nil |
| 35 | Chain204 | RRLIWRRFKWLR | 1 | 0.889 | AMP | 0.978 | 97 | 118 | 6 | 5/11 (45%) | gi_59754033 |
| 36 | Chain205 | KRIVRWRTRKR | 0.995 | 0.72 | AMP | 0.956 | 61 | 112 | 7 | 4/11 (36%) | gi_3407606 |
| 37 | Chain206 | KRIVRWRWRKR | 1 | 0.787 | AMP | 0.912 | 61 | 164 | 7 | 5/11 (45%) | gi_59754033 |
| 38 | Chain207 | KRIVRWRKLKRK | 0.999 | 0.8415 | AMP | 0.943 | 89 | 90 | 8 | 6/11 (54%) | CAMPSQ3545 |
| 39 | Chain208 | WRILRWRKLKR | 1 | 0.9165 | AMP | 0.984 | 106 | 110 | 6 | 5/11 (45%) | CAMPSQ3545 |
| 40 | Chain209 | WRIVRWRKLKR | 1 | 0.9055 | AMP | 0.971 | 97 | 67 | 6 | 6/11 (54%) | CAMPSQ3545 |
| 41 | Chain210 | WRIVQWRKLKR | 0.999 | 0.896 | AMP | 0.844 | 97 | 15 | 5 | 4/11 (36%) | gi_59754101 |
| 42 | Chain211 | KRIVRRRTFKR | 1 | 0.6455 | AMP | 0.999 | 61 | 162.35 | 7 | 6/11 (54%) | gi_75999237 |
| 43 | Chain212 | KRWRKWRLFKR | 1 | 0.803 | AMP | 0.95 | 35 | 106 | 7 | 5/11 (45%) | gi_74472319 |
| 44 | Chain213 | NRIVLLRTFKR | 0.752 | 0.6575 | AMP | 0.983 | 132 | 28 | 4 | No hits | nil |
| 45 | Chain214 | NRIVKKRTFKR | 0.937 | 0.6525 | AMP | 0.983 | 132 | 28 | 4 | 6/11 (54%) | CAMPSQ3535 |
| 46 | Chain215 | RKIVKRRTFKR | 0.997 | 0.672 | AMP | 0.998 | 61 | 99 | 7 | No hits | nil |
| 47 | Chain216 | RKIVWWRTFKR | 0.997 | 0.8025 | AMP | 0.963 | 61 | 20 | 5 | 4/11 (35%) | gi_62788246 |
| 48 | Chain217 | RLIVRRRTFKR | 0.999 | 0.678 | AMP | 0.998 | 97 | 132 | 6 | No hits | nil |
| 49 | Chain218 | RRIVRKKTFKR | 0.997 | 0.652 | AMP | 0.968 | 61 | 80 | 7 | 6/11 (54%) | gi_75999276 |
| 50 | Chain219 | RRIVWRRTFKR | 1 | 0.6675 | AMP | 0.977 | 61 | 132 | 6 | 4/11 (36%) | CAMPSQ3545 |
| 51 | Chain220 | RWIVQRRTFKR | 1 | 0.679 | AMP | 0.986 | 61 | 184 | 6 | No hits | nil |
| 52 | Chain221 | RVIVRRRTFKR | 0.999 | 0.6545 | AMP | 0.996 | 88 | 132 | 6 | No hits | nil |
| 53 | Chain222 | WKIVKKRTRRR | 0.991 | 0.788 | AMP | 0.985 | 61 | 124 | 7 | 4/11 (36%) | gi_74472305 |
| 54 | Chain223 | WRIVRRRTFKR | 0.999 | 0.6965 | AMP | 0.989 | 62 | 132 | 6 | 4/11 (36%) | gi_3407608 |
| 6 | Chain300 | YDKGFGLFKKM | 0.705 | 0.2515 | AMP | 0.11 | 35 | 31 | 2 | No hits | nil |
| 55 | Chain301 | IIKRFRLFKKL | 0.989 | 0.9255 | AMP | 0.999 | 141 | 10 | 5 | 5/11 (45%) | gi_115794206 |
| 56 | Chain302 | ILKRWWLFKKL | 1 | 0.9715 | AMP | 0.996 | 141 | 91 | 4 | 5/11 (45%) | gi_59754119 |
| 57 | Chain303 | IWKRFRLFKKR | 1 | 0.883 | AMP | 0.976 | 71 | 55 | 6 | 5/11 (45%) | gi_115794207 |
| 58 | Chain304 | IWKRFRLFKKW | 1 | 0.955 | AMP | 0.98 | 71 | 25 | 5 | 5/11 (45%) | CAMPSQ754 |
| 59 | Chain305 | RLKWFWLRKLK | 0.999 | 0.95 | AMP | 0.947 | 106 | 14.7 | 5 | 4/11 (36%) | gi_59754121 |
| 60 | Chain306 | RLKRWRLFRKR | 1 | 0.6875 | AMP | 0.917 | 70 | 134 | 7 | 6/11 (54%) | gi_62788246 |
| 61 | Chain307 | RLKWFWLFRKR | 0.999 | 0.8795 | AMP | 0.946 | 106 | 60.7 | 6 | 5/11 (45%) | gi_59754067 |
| 62 | Chain308 | RLKWFLLFRKR | 0.992 | 0.8335 | AMP | 0.94 | 106 | 31 | 5 | 5/11 (45%) | gi_27291218 |
| 63 | Chain309 | WRKWFWLFKKR | 1 | 0.9455 | AMP | 0.995 | 35.4 | 36.2 | 5 | 6/11 (54%) | CAMPSQ354 |
| 64 | Chain310 | KRKWRWLFKKL | 0.999 | 0.8745 | AMP | 0.944 | 70 | 28 | 5 | 6/11 (54%) | CAMPSQ461 |
| 65 | Chain311 | KLKWFWLFKKR | 0.999 | 0.954 | AMP | 0.91 | 70 | 21 | 5 | 4/11 (36%) | gi_10064836 |
| 66 | Chain312 | KLKKFKLFKKR | 0.999 | 0.819 | AMP | 0.96 | 70 | −11.5 | 7 | 8/11 (72%) | gi_115794212 |
| 67 | Chain313 | RLKRFRLFRKRK | 0.999 | 0.722 | AMP | 0.994 | 65 | 56 | 8 | 5/12 (42%) | gi_115794207 |
| 68 | Chain314 | KRKRFRLFKKR | 1 | 0.6525 | AMP | 0.998 | 35 | 84 | 8 | 6/11 (54%) | gi_115794207 |
| 69 | Chain315 | RLKRFRLFKKL | 0.997 | 0.7565 | AMP | 0.982 | 106 | 9.6 | 6 | 5/11 (45%) | gi_115794207 |
| 70 | Chain316 | RRKRFRLFKKM | 0.985 | 0.5865 | AMP | 0.998 | 35 | 106 | 7 | 7/11 (63%) | CAMPSQ114 |
| 71 | Chain317 | RRKRFRLFRRK | 1 | 0.639 | AMP | 0.998 | 36 | 142 | 8 | 7/11 (63%) | gi_112062720 |
| 72 | Chain318 | RWKRFRLFKKR | 1 | 0.7545 | AMP | 0.952 | 35 | 106 | 7 | 5/11 (45%) | gi_115794208 |
| 73 | Chain319 | RWKRFRLFKKW | 1 | 0.8795 | AMP | 0.954 | 35 | 77 | 6 | 5/11 (45%) | gi_115794208 |
| 74 | Chain320 | WKKGFGLFKKM | 0.998 | 0.713 | AMP | 0.967 | 35 | 17 | 4 | 6/11 (54%) | CAMPSQ3086 |
| 75 | Chain321 | WKKRFRLFKKL | 1 | 0.878 | AMP | 0.905 | 70 | 17 | 6 | 6/11 (54%) | CAMPSQ3086 |
| 76 | Chain322 | WLRRFRLFRRL | 1 | 0.769 | AMP | 0.986 | 106 | 141 | 5 | 6/11 (54%) | gi_62788246 |
| 77 | Chain323 | RLKRFLLFRKRL | 0.996 | 0.687 | AMP | 0.988 | 130 | 56 | 6 | 7/12 (58%) | CAMPSQ2349 |
| 78 | Chain324 | KRKWFWLFKKL | 0.999 | 0.8745 | AMP | 0.944 | 70 | 28 | 5 | 6/11 (54%) | CAMPSQ461 |
| 79 | Chain325 | KLKRFRLFKKR | 0.998 | 0.712 | AMP | 0.977 | 70 | 39 | 7 | 6/11 (54%) | gi_115794210 |

[a]SVM: support vector machines;
[b]RF: random forest;
[c]ANN: artificial neural networks;
[d]DA: discriminant analysis;
[e]Aliphatic index: positively correlated with thermostability;
[f]Instability Index: <40 is considered stable;
[g]CAMP database - <http://www.camp.bicnirrh.res.in>

The antimicrobial activity of the twelve peptides (Met1-Met12) was tested against *S. aureus, E. coli*, and *Verticillium dahliae*. Initial screening was performed by the radial diffusion assay to confirm the antimicrobial activity. Peptides Met1, Met3, Met4, Met5, Met10, Met11 and Met12 were active against *E. coli* (FIG. 3) and Met3, Met10 and Met11 exhibited activity against *S. aureus*, each at the concentration of 100 μg/well. Synergistic effect of the peptides was also tested by mixing equimolar concentrations of peptides, but no significant difference in activity was seen. Moderate antifungal activity was observed for Met8 against *Verticillium dahliae* (data not shown). Minimal inhibitory concentration (MIC) assays were carried out for all samples against *E. coli* and *S. aureus*. Met11 was active at the concentration of 95 µM and the rest of the peptides had a MIC of >190 µM. All peptides were predicted to have an alpha helical structure except Met12.

By using rational design techniques, we have designed variants of peptides by incorporating or replacing various amino acids in the original peptides. Thus, we have designed and modified Chain 100, Chain 200 and Chain 300 with tryptophan (W), arginine (R) and lysine (K) at various positions to improve antimicrobial activity (FIGS. 4a-c and 5a-c). In some peptides we have also used other amino acids such as Leucine (L), Cysteine (C), Isoleucine (I), Phenylalanine (F) and Alanine (A). For synthesis, 32 variants and 3 original peptides were selected based on the various parameters such as positive charge, aliphatic index and instability index. Peptides variants were tested by using radial diffusion assay against *Escherichia coli* (ATCC 25922), *Staphylococcus aureus* (ATCC 25923), *Klebsiella pneumoniae* (ATCC 10031) and *Pseudomonas aeruginosa* (ATCC 27853) (FIGS. 6a-c). The zone of inhibition ranged between 10-18 mm for *Escherichia coli* and *Staphylococcus aureus*, 6-18 mm & 8-18 mm for *Pseudomonas aeruginosa* and *Klebsiella pneumonia* respectively (Table 2). For Gentamicin it was between 22-24 mm. Antifungal activity was tested for promising antibacterial peptides (Chains 104, 105, 109, 201, 204, 306, 307, 308, 310) against *Aspergillus flavus* (DSM 1959) and *Penicillium chrysogenum* (DSM 1075). All these peptides has activity at a concentration of 20 µg, Amphotericin B was used as a positive control at 20 µg (FIG. 7).

Minimum inhibition concentrations (MICs) were tested by microbroth dilution method and Chain 104, 105 and 109 inhibited the growth of *Escherichia coli* (ATCC 25922), *Staphylococcus aureus* (ATCC 25923), *Klebsiella pneumoniae* (ATCC 10031) and *Pseudomonas aeruginosa* (ATCC 27853) between 1-8 µg/ml respectively (Tables 3a, 3b and 3c). The membranolytic activities of the peptides were tested by measuring the release of hemoglobin from erythrocytes of fresh blood donated by volunteers. Hemoglobin levels were determined spectrometrically by taking OD at 540 nm by following the protocol of Schmidtchen et al., 2011. The percent hemolysis ranged between 0.1 to 9% indicating that most of these peptides do not have any effect on the host at a concentration of 128 µg/ml (Table 3).

Twelve peptides, Chain 104, Chain 105, Chain 109, Chain 201, Chain 204, Chain 304, Chain 306, Chain 307, Chain 308, Chain 309, Chain 310 and Chain 311 were found to be very active against the four ATCC strains and therefore, were synthesized as D-form amino acids and tested against clinical strains of *E. coli, K. pneumoniae, E. cloacae, P. aeruginosa, Serratia marcescens, Proteus mirabilis, S. pneumoniae, Acinetobacter baumannii, A. johnsonii* and *S. aureus*. Clinical strains of yeasts including *Candida albicans, C. glabrata, C. parapsilosis* and *C. quillermondiae* were also tested with the 12 Chain peptides. The minimum inhibitory concentration (MICs) varied between these peptides and are presented in Tables 4a, 4b, 4c and 5a, 5b, 5c. Peptides Chain 105, 201 and 308 are broad spectrum antimicrobials with MICs between 0.5-32 µg/ml against all the bacteria and yeasts tested, except *Serratia marcescens* and *Proteus mirabilis*, against which the MICs were between 64-128 µg/ml. Peptide Chain 306 has narrow spectrum activity against *E. coli* at 1 µg/ml and for the rest of the bacterial strains at >32 µg/ml (FIG. 10).

Peptides Chain 104, Chain 105, Chain 201, Chain 308, Chain 310 were tested against antibiotic-sensitive strains of *S. aureus* RN4220 and methicillin resistant strains of *S. aureus* COL (MRSA). Chain peptides comprising of either L- or D-form amino acids were tested against these bacteria, and the D-form peptides were found have better activity compared to L-form (Table 6). Synergistic activity of chain peptides along with Ertapenem (4 µg/ml) was tested to know whether it will influence the activity against MRSA strains. All the Chain peptides were found to have antibacterial activity against MRSA strains with MICs at the range of 0.03 to 4 µg/ml. Chain 310 has the best antibacterial activity against the MRSA strains with a MIC of 0.06 & 0.03 µg/ml along with Ertapenem (4 µg/ml) for both forms of L and D-peptides (Table 6).

Many antimicrobial peptides (AMPs) have broad spectrum antimicrobial activity against clinical strains of bacteria and fungi. Antimicrobial peptides form secondary structures by electrostatic interactions with bacterial membranes by a salt-sensitive step. Therefore high salt concentrations in the human body fluids can deactivate many AMPs and it is essential to develop salt-tolerant AMPs for applications in healthcare. However, it is well known that physiological condition, pH, temperature and high salt concentrations will influence the activity of these peptides. We have evaluated pH, salt- and thermostability of Chain 104, 105, 201, 204, 306 and 308 and have found that these peptides are not hindered by pH or temperature even upto 45° C. for over 14 days (FIGS. 8 & 9). However, there is a 2-fold increase in MIC values of Chain 104, 105, 201, 204, 306 and 308 upon using 200 mM NaCl concentration.

Electron microscopy studies were needed to know the AMP mechanism of action on the cells upon treatment with 5× MICs on the cell surface, as well as the intracellular alterations. AMPs typically cause multiple stresses on the cell membranes even at low concentrations. *E. coli* has a complex cell structure with cytoplasmic membrane (7 nm), peptidoglycan layer (7-8 nm) and an outer membrane (10-15 nm). Antibiotic resistance of *E. coli* is due to the presence of inner peptidoglycan along with the outer membrane. Upon incubation with Chain peptides (105, 201, 308), almost all *E. coli* cells had lost their rod-shaped structural integrity, and accumulation of granular structures, bubble-like structure protruded from cell surface and distortions were seen in cells (FIG. 11). The interaction of the Chain peptides with *S. aureus* lipid bilayer can be seen with an expansion of membrane area. We also observed spreading of cytoplasmic membrane and spherical mesosomes as intracellular bilayer membranes and mesosome-like structures formed within the cells.

Catheter-associated infections were initiated by the planktonic bacterial cells adherence to the biomaterial surface by colonization and biofilm formation. Catheters immobilized with Chain 201 or Chain 105 posed excellent antimicrobial activity against *E. coli* and *S. aureus*. A reduction of more than 70% and 30% of living cells of *S. aureus* and *E. coli* was observed, respectively (FIG. 12).

TABLE 2a

Antibacterial activity of peptide variants by radial diffusion method. Inhibition zone is provided in millimeters for respective bacterial pathogens.

| | Inhibition zone (mm)* | | | |
|---|---|---|---|---|
| Peptides | Escherichia coli | Staphylococcus aureus | Pseudomonas aeruginosa | Klebsiella pneumoniae |
| Chain200 | — | — | — | — |
| Chain201 | 16 | 15 | 15 | 14 |

TABLE 2a-continued

Antibacterial activity of peptide variants by radial diffusion method. Inhibition zone is provided in millimeters for respective bacterial pathogens.

| Peptides | Escherichia coli | Staphylococcus aureus | Pseudomonas aeruginosa | Klebsiella pneumoniae |
|---|---|---|---|---|
| Chain202 | — | — | — | — |
| Chain203 | 16 | 8 | 5 | 10 |
| Chain204 | 18 | 15 | 18 | 15 |
| Chain205 | 6 | 5 | — | — |
| Chain206 | 14 | 10 | — | — |
| Chain207 | — | — | — | — |
| Chain208 | 15 | 12 | 10 | 12 |
| Chain209 | 14 | 11 | — | 8 |
| Chain210 | 13 | 10 | — | 6 |
| Gentamycin | 22 | 24 | 24 | 22 |

Test concentration: Gentamycin - 5 µg; Peptides - 50 µg
*Escherichia coli* (ATCC 25922), *Staphylococcus aureus* (ATCC 25923), *Klebsiella pneumoniae* (ATCC 10031) and *Pseudomonas aeruginosa* (ATCC 27853)
*Values in diameter including the wells.

TABLE 2b

Antibacterial activity of peptide variants by radial diffusion method. Inhibition zone is provided in millimeters for respective bacterial pathogens.

| Peptides | Escherichia coli | Staphylococcus aureus | Pseudomonas aeruginosa | Klebsiella pneumoniae |
|---|---|---|---|---|
| Chain200 | — | — | — | — |
| Chain201 | 16 | 15 | 15 | 14 |
| Chain202 | — | — | — | — |
| Chain203 | 16 | 8 | 5 | 10 |
| Chain204 | 18 | 15 | 18 | 15 |
| Chain205 | 6 | 5 | — | — |
| Chain206 | 14 | 10 | — | — |
| Chain207 | — | — | — | — |
| Chain208 | 15 | 12 | 10 | 12 |
| Chain209 | 14 | 11 | — | 8 |
| Chain210 | 13 | 10 | — | 6 |
| Gentamycin | 22 | 24 | 24 | 22 |

Test concentration: Gentamycin - 5 µg; Peptides - 50 µg
*Escherichia coli* (ATCC 25922), *Staphylococcus aureus* (ATCC 25923), *Klebsiella pneumoniae* (ATCC 10031) and *Pseudomonas aeruginosa* (ATCC 27853)
*Values in diameter including the wells.

TABLE 2c

Antibacterial activity of peptide variants by radial diffusion method. Inhibition zone is provided in millimeters for respective bacterial pathogens.

| Peptides | Escherichia coli | Staphylococcus aureus | Pseudomonas aeruginosa | Klebsiella pneumoniae |
|---|---|---|---|---|
| Chain300 | — | — | — | — |
| Chain301 | 12 | 10 | 5 | 10 |
| Chain302 | 12 | 12 | 10 | — |
| Chain303 | 12 | 10 | 4 | — |
| Chain304 | 14 | 16 | 16 | 11 |
| Chain305 | 15 | 12 | 15 | 11 |
| Chain306 | 12 | 8 | 9 | — |
| Chain307 | 19 | 20 | 20 | 17 |
| Chain308 | 19 | 20 | 20 | 18 |
| Chain309 | 11 | 10 | 10 | 11 |
| Chain310 | 17 | 15 | 20 | 16 |
| Chain311 | 13 | 14 | 18 | 13 |
| Chain312 | — | — | — | — |
| Chain313 | 8 | 7 | 14 | — |
| Gentamycin | 22 | 24 | 24 | 22 |

Test concentration: Gentamycin - 5 µg; Peptides - 50 µg
*Escherichia coli* (ATCC 25922), *Staphylococcus aureus* (ATCC 25923), *Klebsiella pneumoniae* (ATCC 10031) and *Pseudomonas aeruginosa* (ATCC 27853)
*Values in diameter including the wells.

TABLE 3a

Minimum inhibitory concentration of different peptide variants tested against 4 bacterial pathogens. Hemolytic activity of the peptides was tested at 128 µg/ml and percent hemolysis is presented.

| | Minimum inhibitory concentration (µg/ml) | | | | |
|---|---|---|---|---|---|
| | Escherichia coli (ATCC 25922) | Staphylococcus aureus (ATCC 25923) | Klebsiella pneumoniae (ATCC 10031) | Pseudomonas aeruginosa (ATCC 27853) | % Hemolysis* |
| Chain100 | >128 | >128 | >128 | >128 | 0.4 |
| Chain101 | >128 | >128 | >128 | >128 | 4.1 |
| Chain102 | >128 | >128 | >128 | >128 | 5.0 |
| Chain103 | >128 | >128 | >128 | >128 | 0.7 |
| Chain104 | 8 | 32 | 16 | 0.25 | 0.5 |
| Chain105 | 2 | 2 | 1 | 2 | 0.2 |
| Chain106 | >128 | >128 | >128 | 64 | 0.9 |
| Chain107 | 64 | >128 | >128 | >128 | 0.1 |
| Chain108 | >128 | >128 | >128 | >128 | 0.5 |
| Chain109 | 8 | 8 | 8 | 16 | 3.8 |
| Gentamicin | 1 | 0.25 | 0.25 | 0.25 | — |
| Tetracycline | 8 | 2 | 2 | 32 | — |

*Tested at 128 µg/ml

TABLE 3b

Minimum inhibitory concentration of different peptide variants tested against 4 bacterial pathogens. Hemolytic activity of the peptides was tested at 128 µg/ml and percent hemolysis is presented.

| | Minimum inhibitory concentration (µg/ml) | | | | |
|---|---|---|---|---|---|
| | Escherichia coli (ATCC 25922) | Staphylococcus aureus (ATCC 25923) | Klebsiella pneumoniae (ATCC 10031) | Pseudomonas aeruginosa (ATCC 27853) | % Hemolysis* |
| Chain200 | >128 | >128 | >128 | >128 | 0.62 |
| Chain201 | 2 | 4 | 8 | 8 | 0.56 |
| Chain202 | >128 | >128 | >128 | 1 | 0.56 |
| Chain203 | 32 | >128 | >128 | >128 | 0.46 |
| Chain204 | 2 | 16 | 32 | 4 | 0.55 |
| Chain205 | 64 | >128 | >128 | >128 | 0.60 |
| Chain206 | 16 | >128 | >128 | >128 | 0.29 |
| Chain207 | >128 | >128 | >128 | >128 | 0.33 |
| Chain208 | 32 | >128 | >128 | 32 | 2.01 |
| Chain209 | 64 | >128 | >128 | >128 | 9.01 |
| Chain210 | >128 | >128 | >128 | >128 | 8.61 |
| Gentamycin | 1 | 0.25 | 0.25 | 0.25 | — |
| tetracyclin | 8 | 2 | 2 | 32 | — |

*Tested at 128 µg/ml

TABLE 3c

Minimum inhibitory concentration of different peptide variants tested against 4 bacterial pathogens. Hemolytic activity of the peptides was tested at 128 µg/ml and percent hemolysis is presented.

| | Minimum inhibitory concentration (µg/ml) | | | | |
|---|---|---|---|---|---|
| | Escherichia coli (ATCC 25922) | Staphylococcus aureus (ATCC 25923) | Klebsiella pneumoniae (ATCC 10031) | Pseudomonas aeruginosa (ATCC 27853) | % Hemolysis* |
| Chain300 | >128 | >128 | >128 | >128 | 6.81 |
| Chain301 | 64 | >128 | >128 | 64 | 0.24 |
| Chain302 | >128 | 128 | >128 | 16 | 0.44 |
| Chain303 | 64 | >128 | >128 | >128 | 0.22 |
| Chain304 | 16 | 32 | 64 | 8 | 0.34 |
| Chain305 | 128 | 64 | 64 | 16 | 0.43 |
| Chain306 | 8 | 2 | >128 | 64 | 0.04 |
| Chain307 | 8 | 4 | 16 | 1 | 0.22 |
| Chain308 | 1 | 4 | 4 | 2 | 0.32 |
| Chain309 | 32 | 32 | 64 | 8 | 0.09 |
| Chain310 | 4 | 8 | 16 | 1 | 3.69 |
| Chain311 | 16 | 32 | 32 | 8 | 1.18 |
| Chain312 | >128 | >128 | >128 | >128 | 4.87 |
| Chain313 | 32 | >128 | >128 | 64 | 5.40 |
| Gentamycin | 1 | 0.25 | 0.25 | 0.25 | — |
| tetracyclin | 8 | 2 | 2 | 32 | — |

*Tested at 128 µg/ml

TABLE 4a

Minimum inhibitory concentration of peptide variants as determined by microdilution method.

| Bacteria* | Strains | Chain104 | Chain105 | Chain109 |
|---|---|---|---|---|
| Escherichia coli | 1 | 4 | 1 | 16 |
| | 2 | 4 | 4 | 4 |
| | 3 | 4 | 1 | 4 |
| | 4 | 4 | 1 | 4 |
| | 5 | 4 | 2 | 4 |
| Klebsiella pneumoniae | 1 | 8 | 4 | 16 |
| | 2 | 4 | 2 | 8 |
| | 3 | 8 | 4 | 8 |
| | 4 | 16 | 4 | 16 |
| | 5 | 4 | 2 | 8 |
| Pseudomonas aeruginosa | 1 | 4 | 4 | 16 |
| | 2 | 2 | 4 | 16 |
| | 3 | 4 | 4 | 16 |
| | 4 | 2 | 4 | 16 |
| | 5 | 1 | 4 | 8 |
| Serratia marcescens | 1 | >128 | 128 | >128 |
| | 2 | >128 | 128 | >128 |
| | 3 | >128 | 128 | >128 |
| | 4 | >128 | 128 | >128 |
| | 5 | 128 | 128 | 64 |

TABLE 4a-continued

Minimum inhibitory concentration of peptide variants as determined by microdilution method.

| Bacteria* | Strains | Chain104 | Chain105 | Chain109 |
|---|---|---|---|---|
| Proteus mirabilis | 1 | >128 | >128 | >128 |
| | 2 | 32 | 32 | 64 |
| | 3 | 128 | 64 | 64 |
| | 4 | >128 | >128 | >128 |
| | 5 | >128 | >128 | >128 |
| Enterobacter cloacae | 1 | 4 | 2 | 4 |
| | 2 | 4 | 2 | 8 |
| | 3 | 8 | 2 | 8 |
| | 4 | 4 | 2 | 8 |
| | 5 | 2 | 1 | 4 |
| Staphylococcus aureus | 1 | 4 | 2 | 2 |
| | 2 | 2 | 2 | 4 |
| | 3 | 4 | 2 | 2 |
| | 4 | 2 | 2 | 2 |
| | 5 | 4 | 2 | 2 |
| Streptococcus pneumoniae | 1 | 4 | 4 | 16 |
| | 2 | 2 | 2 | 8 |
| | 3 | 1 | 2 | 2 |
| | 4 | 4 | 4 | 8 |
| | 5 | 1 | 2 | 8 |
| Acinetobacter baumannii | 1 | 16 | 4 | — |
| | 2 | 8 | 4 | — |
| | 3 | 8 | 4 | — |
| | 4 | 4 | 2 | — |
| | 5 | 8 | 4 | — |
| Acinetobacter johnsonii | 1 | 8 | 4 | — |

*The MIC values are determined by microdilution method using Muller Hinton broth-cation adjusted in presence of 0.02% BSA and 0.2% acetic acid.

TABLE 4b

Minimum inhibitory concentration of peptide variants as determined by microdilution method.

| Bacteria* | Strains | Chain201 | Chain204 |
|---|---|---|---|
| Escherichia coli | 1 | 16 | 8 |
| | 2 | 1 | 1 |
| | 3 | 1 | 1 |
| | 4 | 1 | 1 |
| | 5 | 1 | 1 |
| Klebsiella pneumoniae | 1 | 2 | 8 |
| | 2 | 2 | 4 |
| | 3 | 4 | 16 |
| | 4 | 4 | 4 |
| | 5 | 2 | 2 |
| Pseudomonas aeruginosa | 1 | 4 | 4 |
| | 2 | 4 | 16 |
| | 3 | 4 | 8 |
| | 4 | 2 | 8 |
| | 5 | 2 | 4 |
| Serratia marcescens | 1 | 64 | >128 |
| | 2 | 64 | >128 |
| | 3 | 64 | 128 |
| | 4 | 64 | >128 |
| | 5 | 128 | >128 |
| Proteus mirabilis | 1 | >128 | >128 |
| | 2 | 32 | 32 |
| | 3 | 64 | 64 |
| | 4 | >128 | >128 |
| | 5 | >128 | >128 |
| Enterobacter cloacae | 1 | 1 | 4 |
| | 2 | 2 | 8 |
| | 3 | 2 | 4 |
| | 4 | 2 | 8 |
| | 5 | 1 | 2 |
| Staphylococcus aureus | 1 | 1 | 1 |
| | 2 | 1 | 2 |
| | 3 | 1 | 2 |
| | 4 | 1 | 1 |
| | 5 | 1 | 1 |
| Streptococcus pneumoniae | 1 | 8 | 4 |
| | 2 | 4 | 4 |
| | 3 | 2 | 4 |
| | 4 | 4 | 4 |
| | 5 | 4 | 4 |
| Acinetobacter baumannii | 1 | 4 | 4 |
| | 2 | 4 | 4 |
| | 3 | 4 | 4 |
| | 4 | 4 | 4 |
| | 5 | 4 | 4 |
| Acinetobacter johnsonii | | | |

*The MIC values are determined by microdilution method using Muller Hinton broth-cation adjusted in presence of 0.02% BSA and 0.2% acetic acid.

TABLE 4c

Minimum inhibitory concentration of peptide variants as determined by microdilution method.

| Bacteria* | Strains | Chain304 | Chain306 | Chain307 | Chain308 | Chain309 | Chain310 | Chain311 | Gentamicin |
|---|---|---|---|---|---|---|---|---|---|
| Escherichia coli | 1 | 1 | 1 | 4 | 1 | 0.5 | 4 | 2 | 0.5 |
| | 2 | 16 | 2 | 4 | 0.5 | 32 | 32 | 2 | 0.5 |
| | 3 | 16 | 2 | 4 | 1 | 16 | 16 | 1 | 1 |
| | 4 | 32 | 2 | 2 | 1 | 32 | 16 | 0.5 | 1 |
| | 5 | 32 | 2 | 4 | 1 | 16 | 16 | 1 | 1 |
| Klebsiella pneumoniae | 1 | >128 | 128 | 8 | 4 | 128 | 64 | 8 | 2 |
| | 2 | >128 | >128 | 8 | 4 | 32 | 64 | 8 | 0.25 |
| | 3 | >128 | >128 | 16 | 4 | >128 | 128 | 4 | 2 |
| | 4 | >128 | 64 | 16 | 4 | 32 | 64 | 8 | 2 |
| | 5 | 64 | 64 | 4 | 4 | 128 | 32 | 4 | 4 |
| Pseudomonas aeruginosa | 1 | 32 | 128 | 16 | 8 | 16 | 8 | 16 | 1 |
| | 2 | 64 | >128 | 16 | 8 | 32 | 16 | 8 | 0.5 |
| | 3 | 64 | 128 | 16 | 4 | 16 | 16 | 16 | 0.5 |
| | 4 | 64 | >128 | 8 | 4 | 32 | 8 | 8 | 0.5 |
| | 5 | 16 | 128 | 8 | 4 | 8 | 4 | 4 | 0.25 |
| Serratia marcescens | 1 | >128 | >128 | >128 | 128 | >128 | >128 | >128 | 1 |
| | 2 | >128 | >128 | >128 | 128 | >128 | >128 | >128 | 2 |
| | 3 | >128 | >128 | 128 | 64 | >128 | >128 | >128 | 1 |
| | 4 | >128 | >128 | >128 | >128 | >128 | >128 | >128 | 1 |
| | 5 | >128 | >128 | >128 | 128 | >128 | >128 | >128 | 1 |

TABLE 4c-continued

Minimum inhibitory concentration of peptide variants as determined by microdilution method.

| Bacteria* | Strains | Chain304 | Chain306 | Chain307 | Chain308 | Chain309 | Chain310 | Chain311 | Gentamicin |
|---|---|---|---|---|---|---|---|---|---|
| *Proteus mirabilis* | 1 | >128 | >128 | >128 | >128 | >128 | >128 | >128 | 2 |
| | 2 | >128 | >128 | 128 | 32 | >128 | >128 | 128 | 2 |
| | 3 | >128 | >128 | 128 | 128 | >128 | >128 | 128 | >128 |
| | 4 | >128 | >128 | >128 | >128 | >128 | >128 | >128 | 8 |
| | 5 | >128 | >128 | >128 | >128 | >128 | >128 | >128 | >128 |
| *Enterobacter cloacae* | 1 | 64 | 64 | 4 | 2 | >128 | 128 | 4 | 0.25 |
| | 2 | 64 | 64 | 8 | 2 | 128 | 64 | 4 | 0.25 |
| | 3 | 128 | 32 | 4 | 2 | 64 | 16 | 4 | 0.25 |
| | 4 | 128 | 16 | 4 | 2 | 64 | 8 | 4 | 0.25 |
| | 5 | 32 | 16 | 4 | 2 | 32 | 16 | 2 | 0.25 |
| *Staphylococcus aureus* | 1 | 32 | 16 | 2 | 1 | 8 | 8 | 1 | 0.5 |
| | 2 | 32 | 32 | 2 | 2 | 16 | 16 | 1 | 0.5 |
| | 3 | 16 | 32 | 2 | 1 | 8 | 8 | 1 | 0.5 |
| | 4 | 16 | 16 | 2 | 2 | 8 | 8 | 1 | 0.5 |
| | 5 | 16 | 8 | 2 | 2 | 8 | 4 | 1 | 0.5 |
| *Streptococcus pneumoniae* | 1 | 128 | 64 | 4 | 8 | 64 | 128 | 16 | 2 |
| | 2 | 128 | 64 | 4 | 4 | 64 | 128 | 8 | 2 |
| | 3 | 128 | 64 | 4 | 8 | 64 | 128 | 16 | 2 |
| | 4 | 128 | 128 | 2 | 2 | 64 | 128 | 4 | 2 |
| | 5 | 64 | 64 | 2 | 4 | 64 | 64 | 8 | 1 |
| *Acinetobacter baumannii* | 1 | — | 16 | — | 4 | — | — | — | 0.5 |
| | 2 | — | 32 | — | 4 | — | — | — | 0.25 |
| | 3 | — | 16 | — | 4 | — | — | — | 0.5 |
| | 4 | — | 16 | — | 2 | — | — | — | 0.5 |
| | 5 | — | 8 | — | 2 | — | — | — | 0.25 |
| *Acinetobacter johnsonii* | 1 | — | 16 | — | 4 | — | — | — | 0.25 |

*The MIC values are determined by microdilution method using Muller Hinton broth-cation adjusted in presence of 0.02% BSA and 0.2% acetic acid.

TABLE 5a

Minimum inhibitory concentration of peptide variants tested against clinical yeast strains

| Fungi | Strains | Chain104D | Chain105D | Chain109D |
|---|---|---|---|---|
| *Candida albicans* | 1 | 8 | 32 | 128 |
| | 2 | 8 | 16 | 128 |
| | 3 | 8 | 32 | 128 |
| | 4 | 8 | 32 | 128 |
| | 5 | 8 | 32 | 128 |
| *C. glabrata* | 1 | 8 | 16 | 128 |
| | 2 | 8 | 16 | 128 |
| | 3 | 8 | 8 | 16 |
| | 4 | 16 | 32 | 64 |
| *C. parapsilosis* | 1 | 4 | 8 | 128 |
| | 2 | 4 | 8 | 128 |
| | 3 | 4 | 8 | 128 |
| | 4 | 2 | 4 | 8 |
| *C. quillermondiae* | 1 | 4 | 8 | 128 |

TABLE 5b

Minimum inhibitory concentration of peptide variants tested against clinical yeast strains

| Fungi | Strains | Chain201D | Chain204D |
|---|---|---|---|
| *Candida albicans* | 1 | 16 | 8 |
| | 2 | 8 | 8 |
| | 3 | 8 | 8 |
| | 4 | 16 | 8 |
| | 5 | 8 | 8 |
| *C. glabrata* | 1 | 8 | 4 |
| | 2 | 8 | 8 |
| | 3 | 8 | 32 |
| | 4 | 64 | 32 |
| *C. parapsilosis* | 1 | 8 | 4 |
| | 2 | 8 | 4 |
| | 3 | 8 | 8 |
| | 4 | 8 | 8 |
| *C. quillermondiae* | 1 | 8 | 4 |

TABLE 5c

Minimum inhibitory concentration of peptide variants tested against clinical yeast strains

| Fungi | Strains | Chain304D | Chain306D | Chain307D | Chain308D | Chain309D | Chain310D | Chain311D | Amphotericin B |
|---|---|---|---|---|---|---|---|---|---|
| *Candida albicans* | 1 | 16 | 16 | 16 | 16 | 32 | 16 | 8 | 2 |
| | 2 | 16 | 8 | 16 | 16 | 32 | 16 | 8 | 0.5 |
| | 3 | 16 | 8 | 16 | 16 | 16 | 16 | 8 | 2 |
| | 4 | 16 | 16 | 16 | 16 | 16 | 16 | 16 | 2 |
| | 5 | 32 | 16 | 16 | 16 | 32 | 16 | 16 | 2 |
| *C. glabrata* | 1 | 16 | 8 | 8 | 16 | 32 | 16 | 16 | 4 |
| | 2 | 16 | 8 | 16 | 16 | 64 | 16 | 16 | 4 |
| | 3 | 8 | 16 | 8 | 16 | 4 | 128 | 8 | 2 |
| | 4 | 64 | 32 | 16 | 16 | 128 | 128 | 64 | 4 |
| *C. parapsilosis* | 1 | 64 | 8 | 16 | 8 | 64 | 64 | 16 | 2 |
| | 2 | 64 | 16 | 8 | 8 | 64 | 64 | 8 | 2 |

TABLE 5c-continued

Minimum inhibitory concentration of peptide variants tested against clinical yeast strains

| Fungi | Strains | Chain304D | Chain306D | Chain307D | Chain308D | Chain309D | Chain310D | Chain311D | Amphotericin B |
|---|---|---|---|---|---|---|---|---|---|
|  | 3 | 32 | 16 | 8 | 8 | 32 | 64 | 8 | 2 |
|  | 4 | 16 | 4 | 8 | 4 | 16 | 16 | 8 | 2 |
| C. quillermondiae | 1 | 16 | 4 | 4 | 4 | 8 | 8 | 4 | 2 |

TABLE 6

Minimum inhibitory concentration (MICs) of peptide variants against antibiotic resistant and sensitive strains of S. aureus and synergistic activity with Ertapenem.

| Compound | S. aureus RN4220 | S. aureus COL (MRSA) | S. aureus COL + 4 μg/ml Ertapenem |
|---|---|---|---|
| 104 | >64 μg/ml | >64 μg/ml | 0.25 μg/ml |
| 104 D | 64 μg/ml | 32 μg/ml | 4 μg/ml |
| 105 | >64 μg/ml | >64 μg/ml | 0.5 μg/ml |
| 105 D | 16 μg/ml | 8 μg/ml | 2 μg/ml |
| 201 | 64 μg/ml | 64 μg/ml | 0.5 μg/ml |
| 201 D | 2 μg/ml | 2 μg/ml | 1 μg/ml |
| 308 | >64 μg/ml | >64 μg/ml | 0.5 μg/ml |
| 308 D | 4 μg/ml | 4 μg/ml | 1 μg/ml |
| 310 | >64 μg/ml | >64 μg/ml | 0.06 μg/ml |
| 310 D | >64 μg/ml | >64 μg/ml | <0.03 μg/ml |

*D—D-Amino acids.

REFERENCES

Andersen A. S., Sandvang D., Schnorr K. M., Kruse T., Neve S., Joergensen B., Karlsmark T., and Krogfelt K. A. (2010) A novel approach to the antimicrobial activity of maggot debridement therapy. J Antimicrob Chemother 65, 1646-1654.

Pirttilá, A. M., Kämäräinen, T., Hirsikorpi, M., Jaakola, L., and Hohtola, A. (2001). DNA isolation methods for medicinal and aromatic plants. Plant molecular biology report 19, a-f.

Schmidtchen, A., Rigstad, L., Kasetty, G., Mizuno, H., Rutlands M. W. and Malsten, M. (2011) Membrane selectivity by W-tagging of antimicrobial peptides. Biochem Biophys Acta 1808, 1081-1891.

Van Lith, M., Karala, A. R., Bown, D., Gatehouse, J. A., Ruddock, L. W., Saunders, P. T., and Benham, A. M. (2007). A developmentally regulated chaperone complex for the endoplasmic reticulum of male haploid germ cells. Mol. Biol. Cell 18, 2795-2804.

Wang, G. S., Li, X., and Wang, Z. (2009) APD2: The updated antimicrobial peptide database and its application in peptide design. Nucleic Acids Res. 37, D933-D937.

The invention claimed is:

1. An antimicrobial peptide, comprising any one of synthetically prepared SEQ ID NOs: 55, 58, 59 and 61 to 65 peptide or said antimicrobial peptide defined by a peptide sequence having at least 90 identity to any one of SEQ ID NOs: 55, 58, 59 and 61 to 65.

2. The peptide of claim 1, wherein said peptide is modified in order to increase antimicrobial activity.

3. The peptide of claim 1, comprising any one of SEQ ID NOs: 55, 58, 59 and 61 to 65.

4. The peptide according to claim 1, having an activity against fungi or yeast.

5. The peptide according to claim 1, having an activity against bacteria.

6. A peptide as defined in claim 1 for use in therapy, as an antimicrobial agent.

7. A method of killing or inhibiting growth of microbes, comprising a step of treating said microbes with a peptide according claim 1.

8. The method according to claim 7, wherein the peptide exhibits an activity against bacteria or fungi or both bacteria and fungi.

\* \* \* \* \*